US012384890B2

(12) United States Patent
Sheikhi et al.

(10) Patent No.: US 12,384,890 B2
(45) Date of Patent: Aug. 12, 2025

(54) METHODS FOR FABRICATING MODULAR HYDROGELS FROM MACROMOLECULES WITH ORTHOGONAL PHYSICO-CHEMICAL RESPONSIVITY

(71) Applicant: The Regents of the University of California, Oakland, CA (US)

(72) Inventors: Amir Sheikhi, State College, PA (US); Dino Di Carlo, Los Angeles, CA (US); Alireza Khademhosseini, Los Angeles, CA (US); Joseph de Rutte, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1055 days.

(21) Appl. No.: 17/279,283

(22) PCT Filed: Oct. 18, 2019

(86) PCT No.: PCT/US2019/056949
§ 371 (c)(1),
(2) Date: Mar. 24, 2021

(87) PCT Pub. No.: WO2020/146031
PCT Pub. Date: Jul. 16, 2020

(65) Prior Publication Data
US 2021/0403649 A1 Dec. 30, 2021

Related U.S. Application Data

(60) Provisional application No. 62/747,562, filed on Oct. 18, 2018.

(51) Int. Cl.
*C08J 3/075* (2006.01)
*A61L 27/22* (2006.01)
(Continued)

(52) U.S. Cl.
CPC ............. *C08J 3/075* (2013.01); *A61L 27/222* (2013.01); *A61L 27/52* (2013.01); *A61L 27/56* (2013.01); *C08J 3/24* (2013.01); *A61L 2400/06* (2013.01)

(58) Field of Classification Search
None
See application file for complete search history.

(56) References Cited

U.S. PATENT DOCUMENTS

| 6,017,496 A | 1/2000 | Nova et al. |
| 9,084,546 B2 | 7/2015 | Richardson-Burns et al. |
| (Continued) |

OTHER PUBLICATIONS

PCT International Search Report & Written Opinion dated Jun. 19, 2020 for PCT Application No. PCT/US19/56949.
(Continued)

*Primary Examiner* — Dominic Lazaro
(74) *Attorney, Agent, or Firm* — GATES & COOPER LLP

(57) ABSTRACT

Despite the significant advances in designing injectable bulk hydrogels, the inability to control the pore interconnectivity and decoupling it from the matrix stiffness has tremendously limited the applicability of stiff, flowable hydrogels for 3D cellular engineering. To address this problem, we developed a universal method to convert macromolecules and the like with orthogonal chemical and/or physical responsivity, e.g., thermosensitive macromolecules with chemically-crosslinkable moieties, into annealable building blocks, forming 3D microporous beaded scaffolds in a bottom-up approach. For example, gelatin methacryloyl (GelMA), a widely used biomaterial in tissue engineering, may be converted into physically-crosslinked microbeads using a facile microfluidic approach, followed by flow of the microbead slurry and chemical crosslinking in situ to fabricate microporous beaded GelMA (B-GelMA) scaffolds with interconnected (Continued)

pores, promoting cell functionality and rapid (within minutes) 3D seeding in stiff scaffolds, which are otherwise impossible in the bulk gel counterparts.

12 Claims, 21 Drawing Sheets

(51) Int. Cl.
*A61L 27/52* (2006.01)
*A61L 27/56* (2006.01)
*C08J 3/24* (2006.01)

(56) References Cited

U.S. PATENT DOCUMENTS

| 2002/0040064 | A1 | 4/2002 | Kunz et al. |
| 2009/0269397 | A1 | 10/2009 | Saltzman et al. |
| 2016/0279283 | A1* | 9/2016 | Griffin .................. A61L 26/009 |
| 2017/0368224 | A1 | 12/2017 | Griffin et al. |

OTHER PUBLICATIONS

Extended European Search Report dated Jun. 15, 2022 for European Patent Application No. 19908337.9.
European Communication pursuant to Article 94(3) EPC dated Jul. 21, 2023 for European Application No. 19908337.9.
Catoira et al., "Overview of natural hydrogels for regenerative medicine applications". Journal of Materials Science: Materials in Medicine (2019) 30:115.

* cited by examiner

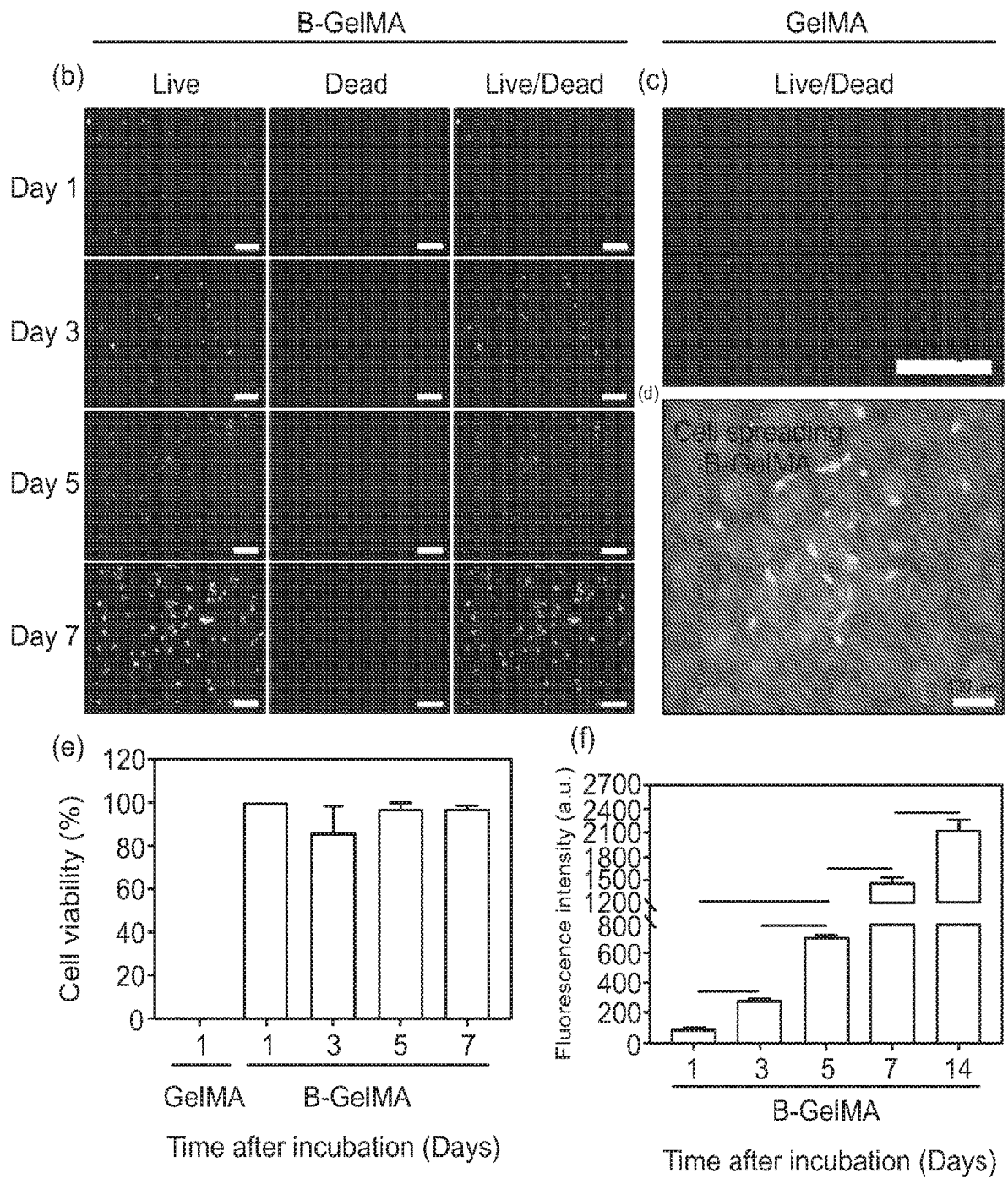
FIG. 5B-F

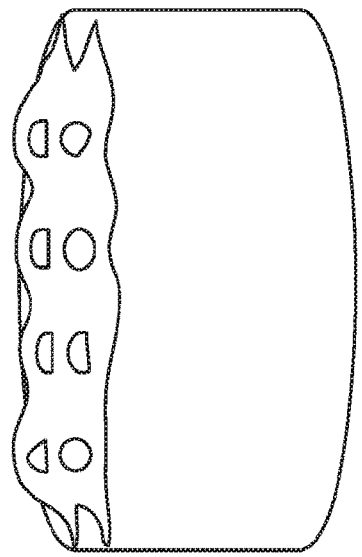
GelMA
versus
FIG. 6A
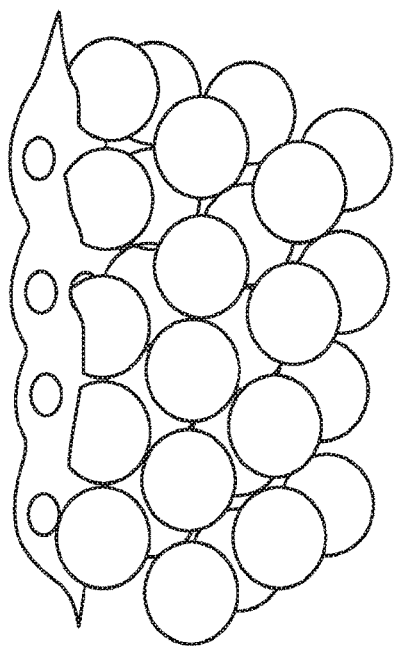
B-GelMA
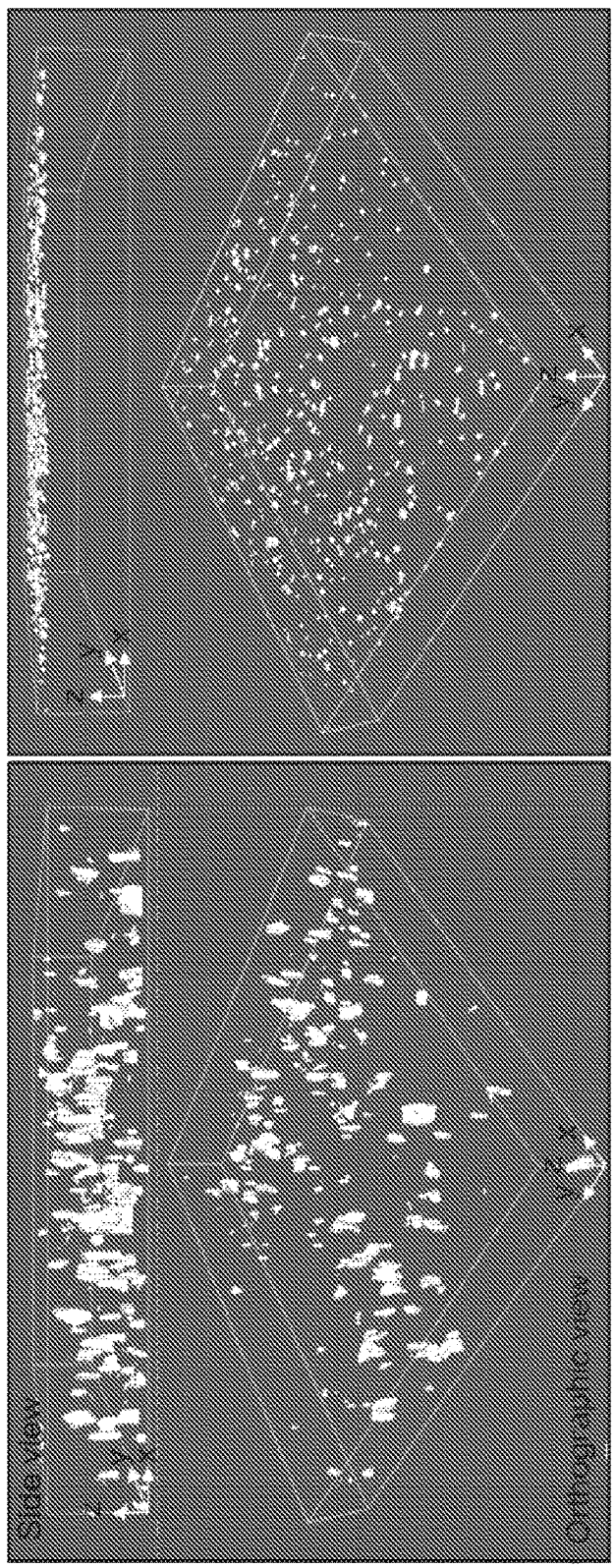
FIG. 6B

US 12,384,890 B2

METHODS FOR FABRICATING MODULAR HYDROGELS FROM MACROMOLECULES WITH ORTHOGONAL PHYSICO-CHEMICAL RESPONSIVITY

CROSS REFERENCE TO RELATED APPLICATIONS

This application claims the benefit under 35 U.S.C. Section 119(e) of and commonly-assigned U.S. Provisional Patent Application Ser. No. 62/747,562, filed on Oct. 18, 2018, and entitled "METHODS FOR FABRICATING MODULAR HYDROGELS FROM MACROMOLECULES WITH ORTHOGONAL PHYSICO-CHEMICAL RESPONSIVITY" which application is incorporated by reference herein.

STATEMENT OF GOVERNMENT SUPPORT

This invention was made with government support under Grant Number N00014-16-1-2997, awarded by the U.S. Navy, Office of Naval Research. The government has certain rights in the invention.

TECHNICAL FIELD

The invention relates to methods and materials useful to fabricate hydrogels.

BACKGROUND OF THE INVENTION

Hydrogels, hydrophilic polymer networks that may absorb water up to several orders of magnitude higher than their dry mass, have secured a promising role in developing cell microenvironments for tissue engineering [1-7]. Common strategies to build hydrogel scaffolds for biomedical applications encompass chemical crosslinking and physical bonding [8,9]. Chemical crosslinking, achieved through covalent bond formation, often provides robust, mechanically resilient platforms for cell encapsulation, and physical binding through polymer entanglement, electrostatic interaction, hydrophobic and ionic binding, host-guest interactions, heat activation, hydrogen bonding, and other mechanisms may enable the reversible formation of a polymer network, allowing for controlled delivery of target cells and cargos [11-17].

In the past few decades, significant effort has been devoted to design, synthesize, and engineer hydrogels at the micro- and nanoscale to impart unique properties, such as surface patterns, injectability, and stimuli-responsiveness [17-21]. These properties, despite their benefits, are typically applied to "bulk" hydrogels, wherein one or several types of building blocks (e.g., polymer chains and/or nanoparticles) interact throughout the whole network, leaving no voids or other openings among the constituents at the microscale. Furthermore, to obtain a micron-sized characteristic mesh size $\xi$, the storage modulus of the hydrogel $G' \sim k_B T/\xi^3$ becomes ~order of mPa, an implausibly low modulus, in which random micron-sized pores would also be randomly arranged without interconnectivity. Here, $k_B$ is the Boltzmann constant ($\sim 1.38 \times 10^{-23}$ m$^2$ kg s$^{-2}$ K$^{-1}$), and 7 denotes temperature 1221. On the other hand, stiff hydrogels, often demanded in a variety of tissue engineering applications, including bone and muscle tissue engineering, may not provide a favorable microenvironment for cells, due to the small mesh size, impaired nutrient and oxygen permeation, and the stress exerted to the encapsulated cells during the polymer network formation.

Lack of pore interconnectivity in "bulk" hydrogels, inhibiting effective cell elongation, migration, and polarization has stimulated an immense interest towards developing microporous scaffolds based on small-scale gel building blocks, such as microspheres. To address some of the challenges associated with bulk hydrogels, droplet microfluidic-assisted small-scale gel particle fabrication has emerged for biomedical applications [23]. Recently, microporous annealed particle (MAP) gels have emerged through a two-step chemical reaction cascade, involving (i) the chemical crosslinking of individual micron-sized beads made up of synthetic materials followed by (ii) the chemical annealing of beads into a larger interconnected scaffold. Multi-armed poly(ethylene) glycol-vinyl sulfone microbeads, decorated with arginylglycylaspartic acid (RGD) cell adhesive peptide motifs and tissue adhesive peptides have been crosslinked through the Michael-type addition with cysteine-terminated matrix metalloprotease (MMP)-sensitive peptide sequences [24]. The individually crosslinked beads were annealed via the covalent bonding between the K and Q peptides obtained by activated Factor XIII (FXIIIa).

Hyaluronic acid (HA) has also been used as a platform for producing bead-based hydrogels. Acrylamide-modified HA has been doped with SH-containing pendent peptides, namely Q and K peptides, which was mixed with dithiol matrix metalloproteinase (MMP)-sensitive linker peptide, annealed using FXIIIa and thrombin, star PEG-N-acryloxysuccinimid (NHS), or white light-activated Eosin Y [25]. The chemical annealing methods required up to 90 min to complete, while the light-mediated strategy took place in ~1 min. Host-guest interactions among the beads have been adapted to reduce chemical complexity and impart reversibility to the bead-bead binding, allowing for a shear-thinning behavior. Photoinitiated thiol-ene reaction of norborene-modified HA with a di-thiol crosslinker (dithiothreitol, DTIT) yielded individually-crosslinked beads, which where reversibly annealed using a amantane-cyclodextrin guest-host binding [26]. This technology, however, demands the off-chip UV light curing of individual (non-annealed) beads, which may introduce additional complexity to controlling the shape, stiffness, and homogeneity of the beads. In addition, crosslinking beads in the oil phase is highly prone to oxygen quenching as a result of a sharp oxygen gradient within the beads [27], which may result in heterogenous stiffness.

There is a need in this field of technology for methods and materials capable of, for example, converting thermo-sensitive materials with crosslinkable moieties into bead-based hydrogel scaffolds having interconnected pores.

SUMMARY OF THE INVENTION

As discussed in detail below, we have developed a universal method to convert macromolecules, or other similar materials which can be dissolved or dispersed or suspended in a fluid, with orthogonal physico-chemical responsivity (e.g., thermosensitive macromolecules with chemically-crosslinkable moieties) or other orthogonal double or multi responsivity (e.g., combinations of pH, ions, heat, electric field, magnetic field, enzymes, and other physical and/or chemical stimuli), into annealable building blocks, forming 3D microporous beaded scaffolds in a bottom-up approach. The methods disclosed herein for converting physico-chemically responsive macromolecules to beaded hydrogels provide numerous advantages that are applicable for a broad range of industries, particularly in the biomedical field. Key advantages of the methods and materials disclosed herein include (1) enabling the ability to reversibly stabilize microbeads using a physical crosslinking method, such as tuning temperature, pH, ionic strength, etc., (2) eliminating the necessity of chemical crosslinking of the polymeric beads in oil-water emulsions, which typically results in oxygen-inhibited crosslinking; (3) facilitating the fabrication procedure by eliminating a chemical crosslinking step; (4) extending the fabrication process to a broad range of macromolecules; (5) providing mechanically robust scaffolds (compared to the existing beaded platforms); as well as (6) reducing waste and saving processing energy and costs.

As an exemplary embodiment of the invention, we show that gelatin methacryloyl (GelMA), a widely used biomaterial in tissue engineering, can be converted into physically-crosslinkable microbeads using a facile microfluidic (flow-focusing) approach to generate droplets, followed by incubation of the GelMA drops at 4° C. to physically crosslink them, breaking the emulsion with a demulsifier to bring the gelled drops into an aqueous phase without coalescence, and finally delivering them to a site and chemically crosslinking them in situ to fabricate microporous beaded GelMA (B-GelMA) scaffolds with interconnected pores, promoting cell functionality and rapid (within minutes) 3D seeding in stiff scaffolds, which are otherwise impossible in the bulk gel counterparts. The novel methodology disclosed herein can be used to produce a next generation of modular hydrogels with orthogonal porosity and stiffness made up of a broad range of natural and synthetic biomaterials. The highly desirable physical, mechanical, and biological properties of one working embodiment of the invention, B-GelMA, are further described in the disclosure below.

Embodiments of the invention include, for example, methods of forming a hydrogel having selected material properties at a predetermined site (e.g. a site of tissue trauma or injury in a patient). These methods typically comprise performing a precursor formation process on a composition comprising macromolecules having crosslinkable moieties disposed within a liquid; incubating the liquid so that the macromolecules are physically crosslinked so as to form a gel emulsion; disrupting the gel emulsion so that the liquid comprises an aqueous phase without coalescence of the gel phase; delivering the disrupted gel emulsion to the site; and then chemically crosslinking the disrupted gel emulsion in situ so as to form a hydrogel at the site; wherein this hydrogel comprises a beaded hydrogel scaffold having interconnected pores. In illustrative embodiments of the invention, the precursor formation process in this methodology is a microfluidic process or an emulsification process; and the liquid comprises water, an oil and optionally a surfactant. In certain embodiments of the invention, the method includes combining the disrupted gel emulsion with a crosslinking initiator prior to chemical crosslinking. In some embodiments of the invention, fluid flow in the microfluidic flow-focusing process are controlled so as to form hydrogel beads having a median diameter from about 70 μm to about 115 μm.

In some embodiments of the invention, the methods are selected to produce a hydrogel with interconnected pores designed so that the void fraction of the pores in the beaded hydrogel scaffold is at least 10% or 15% (e.g. from about 10% to about 20%), and/or the median pore diameter of the pores within the beaded hydrogel scaffold is from about 15 μm to about 25 μm.

In some methodological embodiments of the invention, at least one step is performed at a temperature below 10° C. or below 5° C. (e.g. about 4° C.). For example, in some embodiments of the invention, the method includes purifying a beaded hydrogel scaffold precursor composition from an oil with surfactant so as to form an aqueous solution prior to chemical crosslinking, wherein said purifying occurs at a temperature below 10° C. In addition, in certain embodiments of the invention, the temperature of the site in which the microporous beaded hydrogel is disposed (e.g. proximal patient tissue) is controlled to be lower than 20° C., 10° C. or 5° C.

In typical methods of the invention, the macromolecule used to form the hydrogel comprises a polypeptide. In illustrative embodiments of the invention, the macromolecule comprises a hyaluronic acid, an ethylene glycol, a gelatin, a collagen, an elastin, a fibroin or the like. In some embodiments of the invention the macromolecule comprises a methacryloyl moiety or the like as a crosslinkable moiety. In certain embodiments of the invention, a peptide is coupled to the macromolecule, for example a K peptide, a Q peptide, an MMP peptide or the like. Embodiments of the invention can also further comprise seeding mammalian cells within pores in the three-dimensional microporous beaded hydrogel. In some of these embodiments, the method is designed so that the mammalian cells then exhibit an increasing rate of metabolic activity at 3, 5 and/or 7 days post seeding.

Other embodiments of the invention include beaded hydrogel scaffolds having the desirable material characteristics (e.g. interconnected pores etc.) that can be generated, for example, by the methodologies disclosed herein. For example, in some embodiments of the invention, the beaded hydrogel scaffold exhibits a tensile modulus of at least 50, 100 or 200 kPa; and/or exhibits a compression modulus of at least 10, 50 or 100 kPa. In certain embodiments of the invention, the macromolecules comprise polypeptides and these polypeptides comprise at least 10% 15% or 20% w/v of the hydrogel that forms a beaded hydrogel scaffold having interconnected pores. Typically in these embodiments, the void fraction of the hydrogel that forms a beaded hydrogel scaffold having interconnected pores is at least 10% or 15% (e.g. from about 10% to about 20%), and/or the median pore diameter of the pores within the beaded hydrogel scaffold is between 15-25 μm. Optionally, the beaded hydrogel scaffold material having interconnected pores further comprises live mammalian cells.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1(a): Schematic of surfactant-stabilized microbead production from a GelMA pre-polymer solution using a flow-focus microfluidic device, followed by purification in cold water (4° C.) to obtain stable physically-crosslinked GelMA microbeads. The microbeads may readily be crosslinked in the presence of photoinitiator to form an annealed microporous structure using UV light. Other viable crosslinking methods include visible light and redox pair-mediated free-radical polymerization, commonly used to prepare bulk GelMA [36]. FIG. 1(b): Images of the flow-focus microfluidic device, comprising an inlet for the GelMA solution flow, pinching flow (oil/surfactant) inlets, and one outlet flow. The surfactant-stabilized beads were continuously monitored in an oil reservoir, followed by collecting them in a microcentrifuge tube and washing to remove the oil/surfactant. FIG. 1(c): GelMA bead size versus fluid (oil-to-water) flow ratio and GelMA concentration, showing the versatility of the flow-focus technology in generating beads with sizes ~70-115 μm by altering the flow.

FIG. 2(a): time course photographs and associated graphed data (right column) showing stability of GelMA beads is investigated at varying temperatures over time. At 4° C., GelMA is physically crosslinked, allowing for a long-term stability, which enables the facile processing of beads for a myriad of applications, such as crosslinking, annealing, and culturing cells. Increasing the temperature decreases the stability, resulting in the dissolution of beads. Importantly, chemically-crosslinked beads withstand the physiological temperature for at least 24 h. FIG. 2(b): time course photographs and associated graphed data (right column) showing tailored swelling and shrinking of GelMA beads are achieved through regulating the ionic strength gradient inside and outside the microbeads. When the physically-crosslinked beads are loaded with 1×DPBS, they undergo shrinking in 5×DPBS, and when 1×DPBS-loaded beads are incubated in DI water, they swell (T=4° C.). The chemically-crosslinked beads for 120 s do not undergo significant swelling and shrinking (T=37° C.). The scale bars represent 200 μm.

FIGS. 3A-3L. Annealing GelMA microbeads yields beaded GelMA (B-GelMA). FIG. 3(a) photographs showing UV light-mediated annealing of GelMA beads, resulting in intra- and inter-bead crosslinking, forming self-standing microporous B-GelMA scaffolds with a tailored number of packed bead layers. FIG. 3(b) Schematic of sample preparation for tensile and compression moduli characterization. FIG. 3(c): graphed data showing tensile stress versus tensile strain, and FIG. 3(d): tensile moduli of B-GelMA and bulk GelMA, crosslinked using UV light (intensity ~10 mW cm$^{-2}$ for 60 s, 120 s, and 180 s). Note that uncrosslinked beads were characterize as a control. FIG. 3(e): graphed data showing compression stress versus compression strain, and (f) compression moduli of B-GelMA and bulk GelMA, crosslinked as described in (c, d). FIG. 3(g): graphed data showing Atomic force microscopy (AFM) indentation force versus indentation depth for B-GelMA and GelMA. The small indentation depth (~100 nm) enables to probe the stiffness (compression moduli). FIG. 3(h): graphed data showing individual beads as well as the bulk gel surface. Graphed data showing rheological properties of B-GelMA compared to the bulk GelMA in terms of storage FIG. 3(i) and loss FIG. 3 (j) moduli versus angular frequency. Graphed data showing a summary of storage and loss moduli at an angular frequency ~1 rad s$^{-1}$ and strain ~0.1% is presented in FIG. 3(k) and FIG. 3(l), respectively.

FIG. 4(a) 3D confocal projection of B-GelMA scaffolds. Void space is imaged by incubating scaffolds in FITC-labeled dextran. FIG. 4(b) Process overview photographs for pore size analysis. 2D slices were analyzed using a custom-built MATLAB algorithm to detect void spaces between the annealed beads. Void area was converted to circles of equal area to extrapolate equivalent diameter. FIG. 4(c) graphed data showing void space fraction for B-GelMA scaffolds, prepared using varying crosslinking times, i.e., varying matrix stiffness. FIG. 4(d) graphed data showing Median pore diameter of B-GelMA scaffolds versus crosslinking time. The porosity and void fraction of B-GelMA scaffolds are independent of the matrix stiffness. Accordingly, B-GelMA generates a protein-based microporous scaffold with orthogonal porosity and stiffness.

FIGS. 5A-5F. Comparisons of conventional GelMA and beaded GelMA (B-GelMA) embodiments of the invention show that B-GelMA provides a microporous scaffold with independent stiffness and pore size for 3D cell culture. FIG. 5(a) Schematic of 3D cell culture in B-GelMA versus bulk GelMA. FIG. 5(b) Assessment of live (green) and dead (red) cells, showing that the 3D encapsulation of NIH/3T3 fibroblasts in B-GelMA scaffolds with a high polymer concentration (20% w/v) results in high cell viability, excellent adhesion, and significant proliferation, compared to the bulk GelMA FIG. 5(c) in which cells do not survive the first day of culture. Scale bars are 500 μm. FIG. 5(d) Fluorescent microscopy image of cells adhering to the annealed GelMA beads and spreading among them. FIG. 5(e) Cell viability, defined as the number of live cells divided by the total cell number for GelMA and B-GelMA, showing that while GelMA do not support cells, B-GelMA yields ~100% viability within an extended time. FIG. 5(f) Metabolic activity of the cells, measured using the PrestoBlue® assay, showing that B-GelMA affords an ~25-fold increase in the metabolic activity (proliferation) within 14 days. No metabolic activity was observed in the bulk GelMA.

FIGS. 6A-6B. Comparisons of Three-dimensional cell seeding in B-GelMA versus bulk GelMA scaffolds. FIG. 6(a) Schematic of cell seeding experiments wherein a concentrated HUVEC solution is placed on top of the pre-made scaffolds, followed by immediate confocal imaging. FIG. 6(b) HUVECs seeded on top of the B-GelMA readily transfer in the micropores of the scaffold in less than 5 min (left panel), shown in the confocal microscope images; whereas, the bulk GelMA (20% w/v) do not support 3D cell seeding. Image dimensions ~1550 μm×1550 μm×254 μm.

DETAILED DESCRIPTION OF THE INVENTION

Figure 1A:
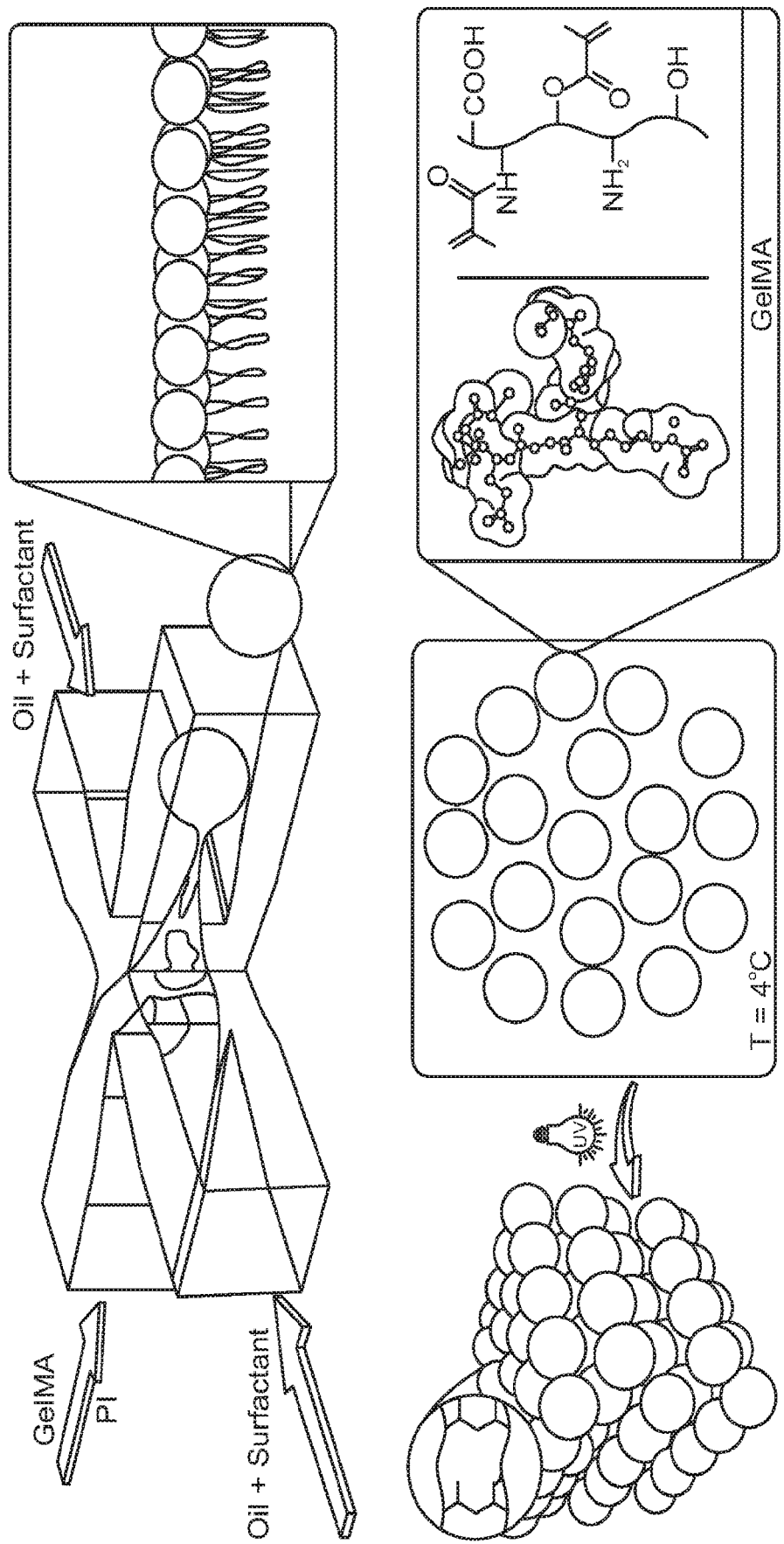
FIGS. 1A-1C. Microfluidic-assisted fabrication of beaded GelMA (B-GelMA).

Many of the techniques and procedures described or referenced herein are well understood and commonly employed using conventional methodology by those skilled in the art. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Despite the significant advances in designing injectable bulk hydrogels, the inability to control the pore interconnectivity and decouple it from matrix stiffness has tremendously limited the applicability of stiff, flowable hydrogels for 3D cellular engineering, e.g., in hard tissue engineering. To this end, a few hydrogel platforms have been fabricated based on annealing microscale gel particles all of which rely on a multi-step chemical modification of the macromolecules. As disclosed herein, in order to address certain challenges in this technology, we have designed a universal method to convert macromolecules with orthogonal physico-chemical responsivity (e.g., thermosensitive macromolecules with chemically-crosslinkable moieties) into annealable building blocks, forming 3D microporous beaded scaffolds in a bottom-up approach. Illustrative materials and methods used in the exemplary embodiments of the invention are discussed in the following sections.

Naturally-derived proteins, such as collagen, elastin, fibroin, fibrin, gelatin (denatured collagen), chitosan and the like hold a remarkable promise for tissue engineering and regenerative medicine. Gelatin methacryloyl (GelMA), synthesized from the methacryloyl modification of gelatin, mimicking the structure of extracellular matrix, has widely been used as a universal multi-responsive scaffold for a broad spectrum of applications, spanning from cell therapy to bioprinting and organoid development. Despite the widespread applications of GelMA, coupled stiffness and porosity has inhibited its applications in 3D cellular engineering wherein a stiff scaffold with large pores is demanded (e.g., at concentrations >10 wt %). Taking advantage of the orthogonal thermo-chemical responsivity of GelMA, we have developed microfluidic-assisted annealable GelMA beads, that are first stabilized by temperature-mediated physical crosslinking, flowed to form a scaffold structure, and then chemically annealed using light to fabricate novel bead-based 3D GelMA scaffolds with high mechanical resilience. We show how beaded GelMA (B-GelMA) provides a self-standing microporous environment with a highly desirable orthogonal void fraction and stiffness, properties that promote cell adhesion, proliferation, and rapid 3D seeding at a high polymer concentration (~20 wt %) that would otherwise be impossible for bulk GelMA. B-GelMA, when, for example, decorated with methacryloyl and arginylglycylaspartic acid (RGD) peptide motifs, does not require additional functionalization for annealing and cell adhesion, providing a versatile biorthogonal platform with orthogonal stiffness and porosity for a myriad of biomedical applications. While B-GelMA is used in illustrative working embodiments of the invention disclosed herein, this technology may be generalized for other thermo-responsive polymers, opening a new horizon for converting bulk hydrogels to beaded hydrogels (B-hydrogels) with decoupled porosity and stiffness.

As noted above, we have developed a facile, universal strategy to convert thermo-sensitive materials with crosslinkable moieties into bead-based scaffolds. As an important model biomaterial for illustrative working embodiments of the invention, we selected a naturally-derived protein, gelatin (denatured collagen), which has a broad range of biomedical applications for tissue engineering and regeneration [28-32], benefitting from built-in RGD peptides, tissue adhesiveness, and thermo-sensitivity. Gelatin, modified with methacrylic anhydride (MA) so as to have methacryloyl crosslinkable moieties, known as GelMA has been widely used as a photocrosslinkable biomaterial to mimic the extracellular matrix (ECM), owing to its inherited properties from collagen, ECM's most abundant structural protein. Unique properties of GelMA, including cell and tissue binding cues, biocompatibility, bioactivity, tunable stiffness and biodegradation, cost effectiveness, and facile synthesis have been explored in a broad spectrum of applications, from tissue engineering to wound healing, cargo delivery, soft lithography and microfabrication [33-36].

We have discovered that GelMA, a photocrosslinkable, thermo-responsive protein derivative, may be produced in the form of microbeads using a flow-focusing microfluidic device and be readily purified from the oil/surfactant coating in a cold aqueous environment without any chemical reaction, in contrast to all of the existing [24-26] annealable beaded platforms, which make use of chemical crosslinking before the purification. The photochemically-active, physically-crosslinked beads can then be chemically crosslinked and annealed to each other through, for example, UV light exposure in the aqueous phase, yielding a beaded GelMA (B-GelMA) scaffold with interconnected pores. We further demonstrate key advantages of the B-GelMA platform over conventional (bulk) GelMA by describing typical mechanical, rheological, and biological characteristics. For example, B-GelMA, in providing orthogonal void fraction and stiffness provides a novel platform for 3D cellular engineering, e.g., fibroblasts and endothelial cells, using stiff matrices (e.g., GelMA ~20% w/v) without compromising cell viability, which may otherwise be impossible. Promising cell viability, adhesion, proliferation, elongation, and seeding inside stiff B-GelMA sets the stage for the next generation of ECM-mimicking microporous cell scaffolds for accelerated healing and regeneration.

Embodiments of the invention include methods of forming a beaded hydrogel scaffold having interconnected pores at a selected site (e.g. site in vivo having diseased or damaged tissue). These methods typically comprise performing a microfluidic flow-focusing process on a composition comprising macromolecules having crosslinkable moieties disposed within a liquid so that droplets are formed. The methods then comprise incubating the droplets so that the macromolecules are physically crosslinked so as to form a gel emulsion; disrupting this gel emulsion with a demulsifier so that the gel droplets remain in an aqueous phase without coalescence; delivering the disrupted gel emulsion to the site; and then chemically crosslinking the disrupted gel emulsion in situ so as to form a three-dimensional microporous beaded hydrogel scaffold having interconnected pores at the site. This methodology allows artisans to form particle hydrogels with porous spaces at a variety of desired sites by using new materials and methodological steps (e.g. physical gelation), followed by covalent crosslinking reactions in situ. As shown below, this methodology has a number of advantages over conventional hydrogel methodologies that employ two separate covalent/chemical crosslinking reactions.

In one illustrative embodiment of the invention, the macromolecules (or other similar materials which can be dissolved or dispersed or suspended in a fluid) that are used in these methods comprises a polypeptide such as a gelatin (i.e. a denatured collagen). The macromolecule can comprise a gelatin, a hyaluronic acid, an ethylene glycol, a collagen, an elastin, a fibroin, a fibrin, a chitosan or the like. In embodiments of the invention, the macromolecules comprise one or more physically and/or chemically crosslinkable moieties. The macromolecules can further include other elements, for example a peptide coupled to the macromolecule (e.g. arginylglycylaspartic acid (RGD) cell adhesive peptides as discussed herein). In some embodiments of the invention, a peptide is coupled to the macromolecule, for example a K peptide, a Q peptide, an MMP peptide or the like (see, e.g. U.S. Patent Publication Nos. 20190151497 and 20190142965, the contents of which are incorporated by reference)

Related embodiments of the invention include beaded hydrogel scaffold compositions formed by a method disclosed herein. As discussed below, in certain embodiments of the invention, the compositions are formed by methods selected to control the material properties of these compositions. For example, in some embodiments of the invention, the beaded hydrogel scaffold exhibits a tensile modulus of at least 50 kPa, 100 kPa or 200 kPa. In another example, the compositions are formed by methods selected to form beaded hydrogel scaffolds that exhibit a compression modulus of at least 10, 50 or 100 kPa. Typically in these embodiments, the void fraction of the hydrogel that forms a beaded hydrogel scaffold having interconnected pores is at least 10% or 15% (e.g. from about 10% to about 20%), and/or the median pore diameter of the pores within the beaded hydrogel scaffold is between 15-25 µm. Other material properties of beaded hydrogel scaffold compositions formed by a method disclosed herein are discussed in the following sections.

Embodiments of the invention include macromolecules that are thermosensitive or exhibit other orthogonal double or multi responsivity (e.g., responsive to combinations of pH, ions, heat, electric field, magnetic field, enzymes, and other physical and/or chemical stimuli etc.). In this context, in typical methods of the invention, at least one step is performed at a temperature below 10° C. or below 5° C. For example, embodiments of the invention can include purifying a beaded hydrogel scaffold precursor composition from oils/surfactants in a cold aqueous environment prior to chemical crosslinking. In some embodiments of the invention, the temperature of the site in which the microporous beaded hydrogel is disposed is further controlled to be lower than 10° C. or 5° C. Optionally the methods can include further steps, for example co-delivering cells with the gel beads such that they occupy pores in the three-dimensional microporous beaded hydrogel that has been disposed at a site of interest.

Figure 1B:
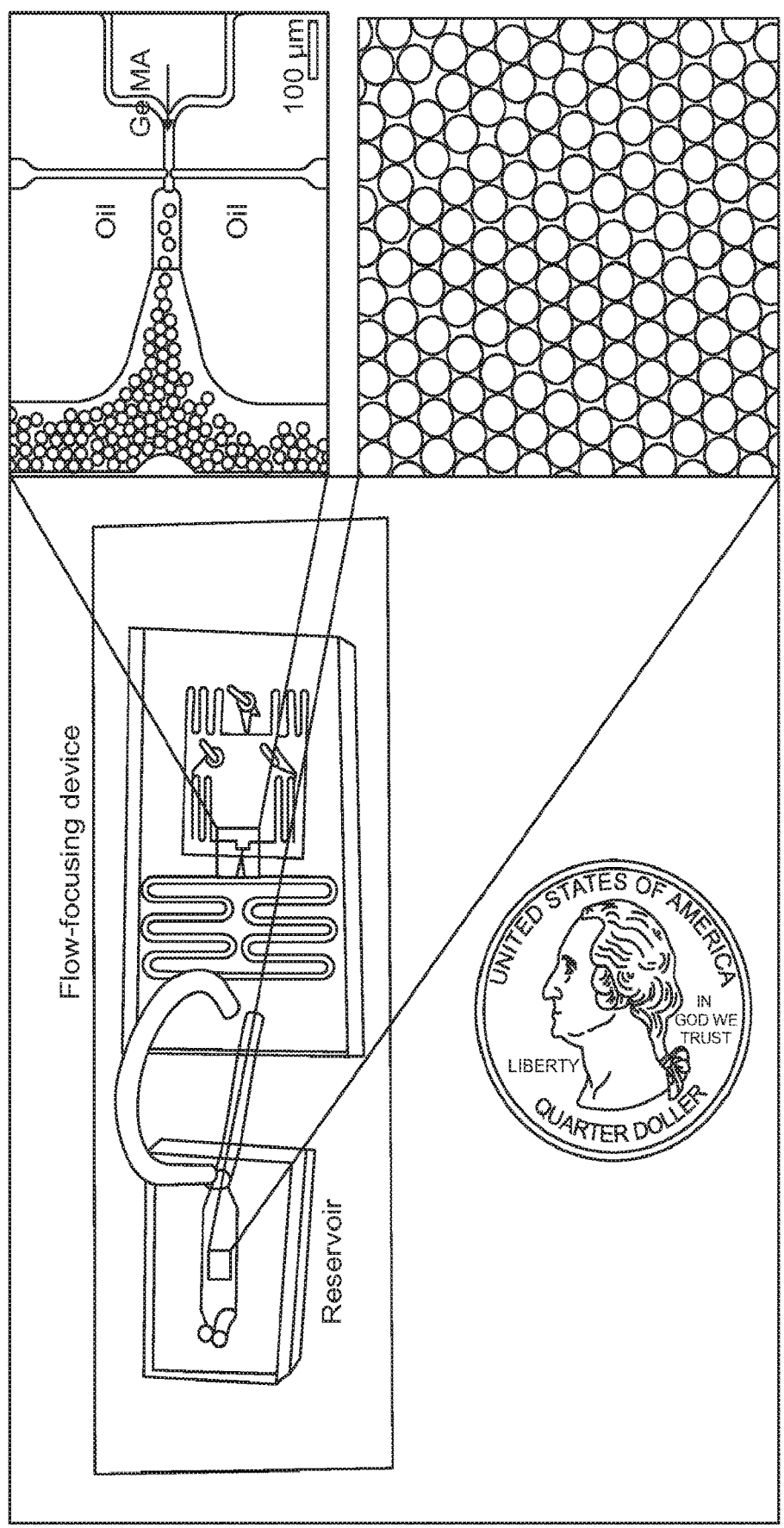

GelMA is used in one illustrative working embodiment of the invention. As discussed below, flow-focusing microfluidic devices are able to effectively produce uniform-sized GelMA microbeads, through pinching the aqueous phase with oil/surfactant flows, as presented schematically in FIG. 1a. The microbeads are then collected as a disperse phase in a continuous oil phase, which may be readily purified by a secondary surfactant after physically crosslinking the beads at 4° C. This initial physical crosslinking step is essential to prevent the dissolution of beads once they are transferred into an aqueous medium, allowing for the elimination of any chemical/light treatment, which have frequently been required in other beaded systems, such as HA [25,26] and poly(ethylene) glycol-vinyl sulfone [24]. The purified beads may undergo subsequent chemical crosslinking using various mechanisms, such as UV-light mediated radical polymerization, forming an annealed 3D scaffold with interconnected microporosity. An illustrative microfluidic setup, comprising a flow-focusing device to generate the GelMA beads and a reservoir for bead collection is shown in FIG. 1b.

Figure 1C:
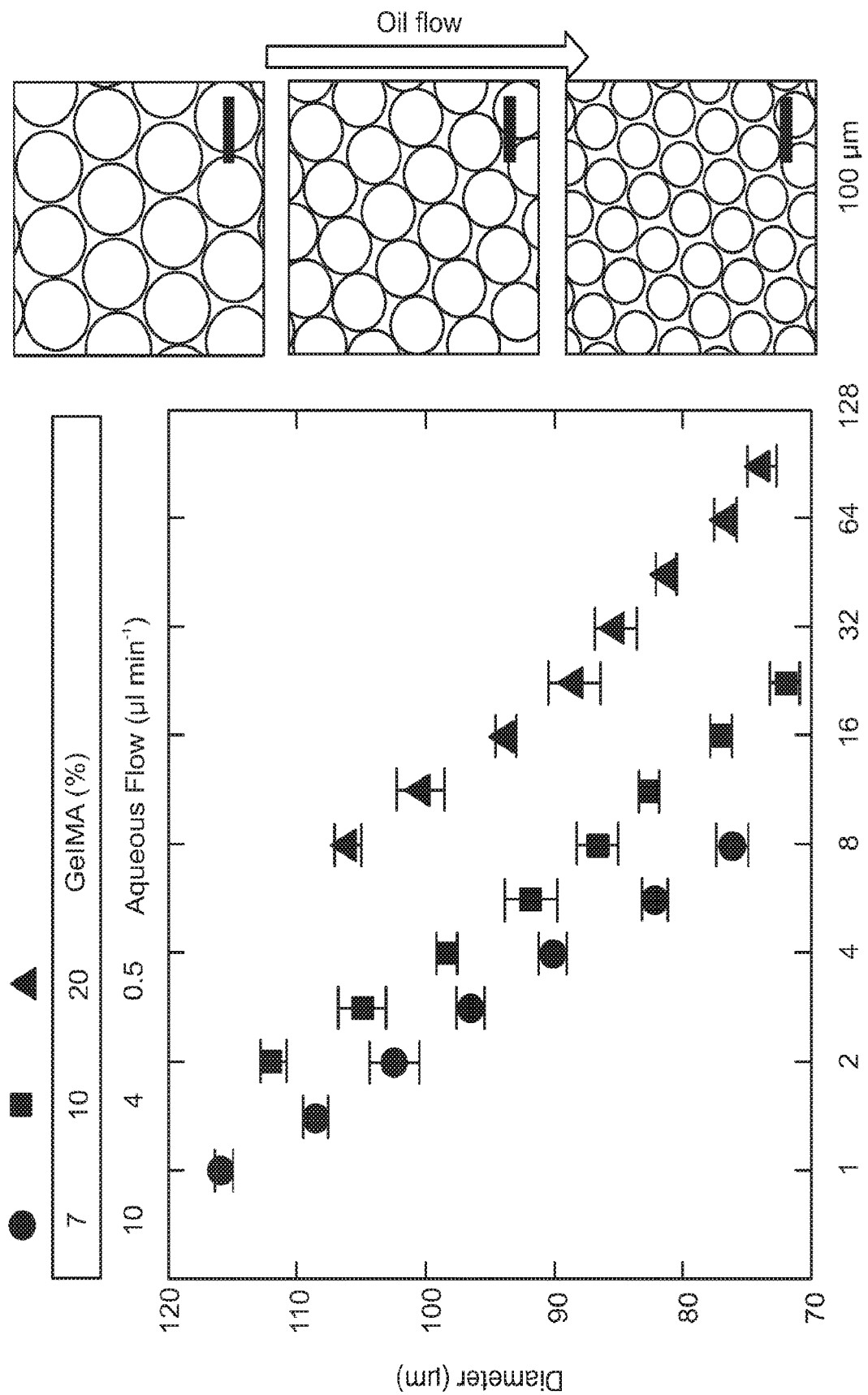

The capability of the microfluidic flow-focusing device to generate GelMA beads with various sizes was explored by changing the GelMA solution (aqueous phase) concentration and the ratio of oil to aqueous flow rates. FIG. 1c presents the size of oil/surfactant-stabilized beads versus the ratio of oil to aqueous flow rates. The beads with 7% (w/v) GelMA content were produced in the range of ~70-120 µm. Smaller beads are generated at higher oil-to-water flow ratios, as a result of increased pinching of the aqueous phase by the oil flow. A flow-focusing device allows for a wide range of bead size production with a simple microfluidic device, only by tuning the flow. Increasing the polymer concentration to 10% and 20% (w/v) slightly decreases the maximum bead size to ~112 and 105 µm, respectively.

Figure 2A:
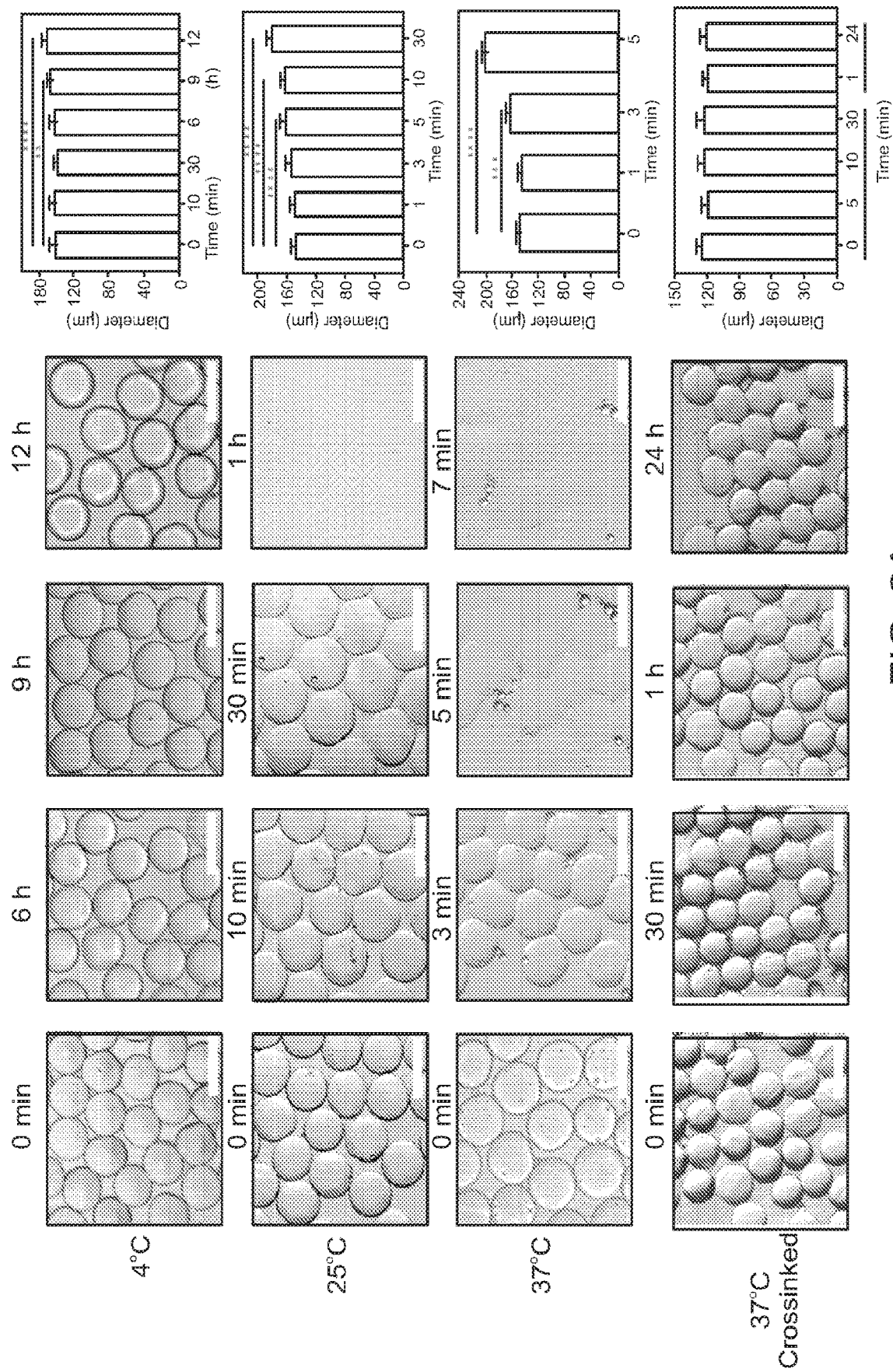
FIGS. 2A-2B. Stability and tailored swelling of GelMA beads.

The stability of the physically-crosslinked beads is a critical factor in designing advanced structures, because it regulates the "allowed" processing time, defined as the maximum time that beads may hold their shape and integrity in an aqueous medium. FIG. 2a presents the time-evolution of physically-crosslinked GelMA microbead sizes (diameter) at various temperatures. At 4° C., the beads hold their shape for up to at least 6 h, showing no significant change in their diameter. After 12 h, the bead diameter increases by ~15%, which may be because of the partial swelling. At room temperature (25° C.), the beads are more susceptible to temperature and can maintain their size only for about 3 min. After 10 min, 30 min, and 1 h, the size increases by ~7%, 20%, and 45% respectively. After 1 h, the beads are highly swollen and ready for dissolution in the medium, which makes them hardly observable. The sensitivity to temperature is more severe at physiological temperature, resulting in a complete dissolution of beads in less than 7 min at 37° C. The results may be explained by the sol-gel transition temperature of GelMA, originated from the temperature-dependent triple helix formation [38] of denatured collagen fibers at 31-32° C. [39]. This behavior is of utmost importance in designing structured scaffolds from the microbead building blocks.

Figure 2B:
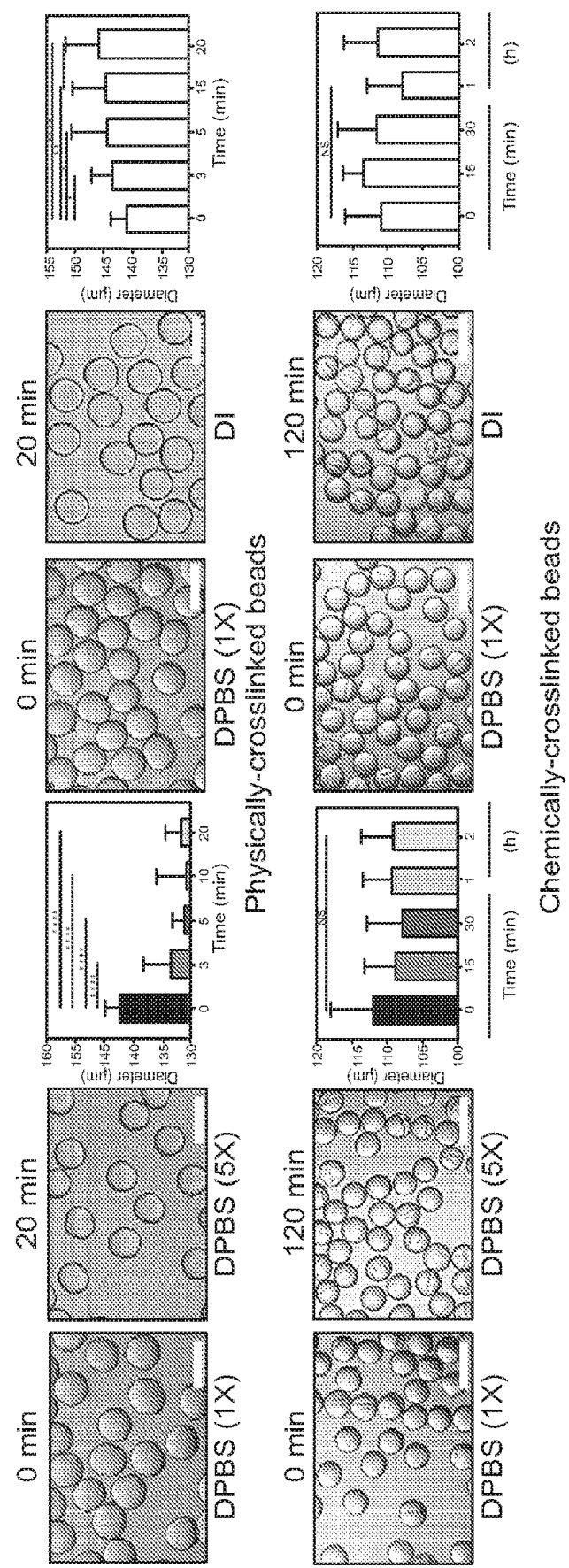

To investigate the stability of chemically-crosslinked microbeads at physiological conditions, a diluted monolayer of beads, containing the PI was exposed to UV light for 2 min in a cold DPBS-PI solution. The crosslinked beads were then incubated at 37° C. for an extended time. The results, presented in FIG. 2a, attest to the excellent stability of the chemically-crosslinked beads at the high temperature. The swelling and shrinkage of the crosslinked beads may be engineered through altering the osmolarity gradient between the beads and media. When the physically-crosslinked beads are loaded with 1×DPBS and placed in a 5×DPBS solution, the osmotic pressure results in the flux of water out of the beads, shrinking the beads (FIG. 2b). Oppositely, when the ionic strength inside the beads is higher than the medium, osmotic flow of water swells the beads. Ion-regulated swelling of GelMA microbeads may be exploited for designing stimuli-responsive carriers. Notably, the chemically-crosslinked beads did not undergo significant swelling or shrinking (FIG. 2b).

Figure 3A:
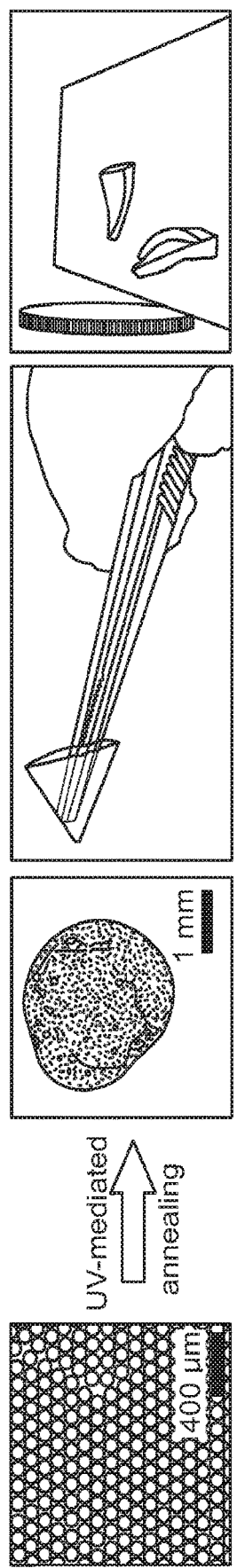

The physically-crosslinked beads may be then assembled into a structurally sound multi-layer scaffold through packing and UV-light mediated chemical crosslinking and annealing. FIG. 3a demonstrates how physically-stabilized packed microbeads in an aqueous solution undergo chemical annealing, forming a densely-packed self-standing microporous scaffold (B-GelMA). The mechanical properties of the scaffolds play an important role in their biomedical applications. For example, injectable scaffolds for cardiac and abdominal tissue engineering must mimic the native tissues and withstand large strains and stresses of the heartbeat and other activities, such as coughing. The stiffness of left ventricle during diastole is ~10-20 kPa and it increases to 200-500 kPa when diastole finishes [40]. Importantly, the pressure in the heart may reach ~19 kPa in a healthy adult [41], and intra-abdominal pressure may be elevated to ~34 kPa [42].

Figure 3B:
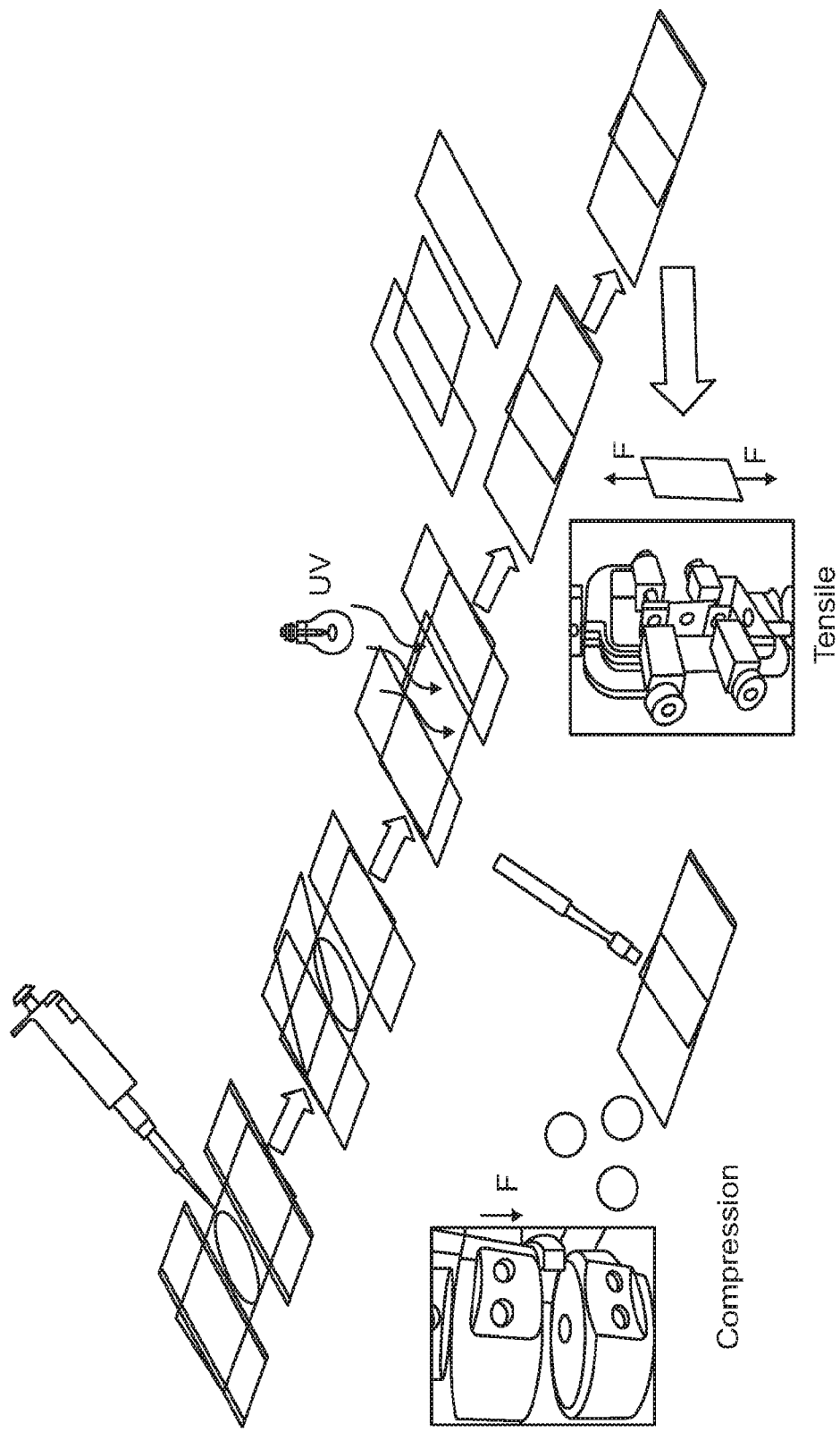
Figure 3C:
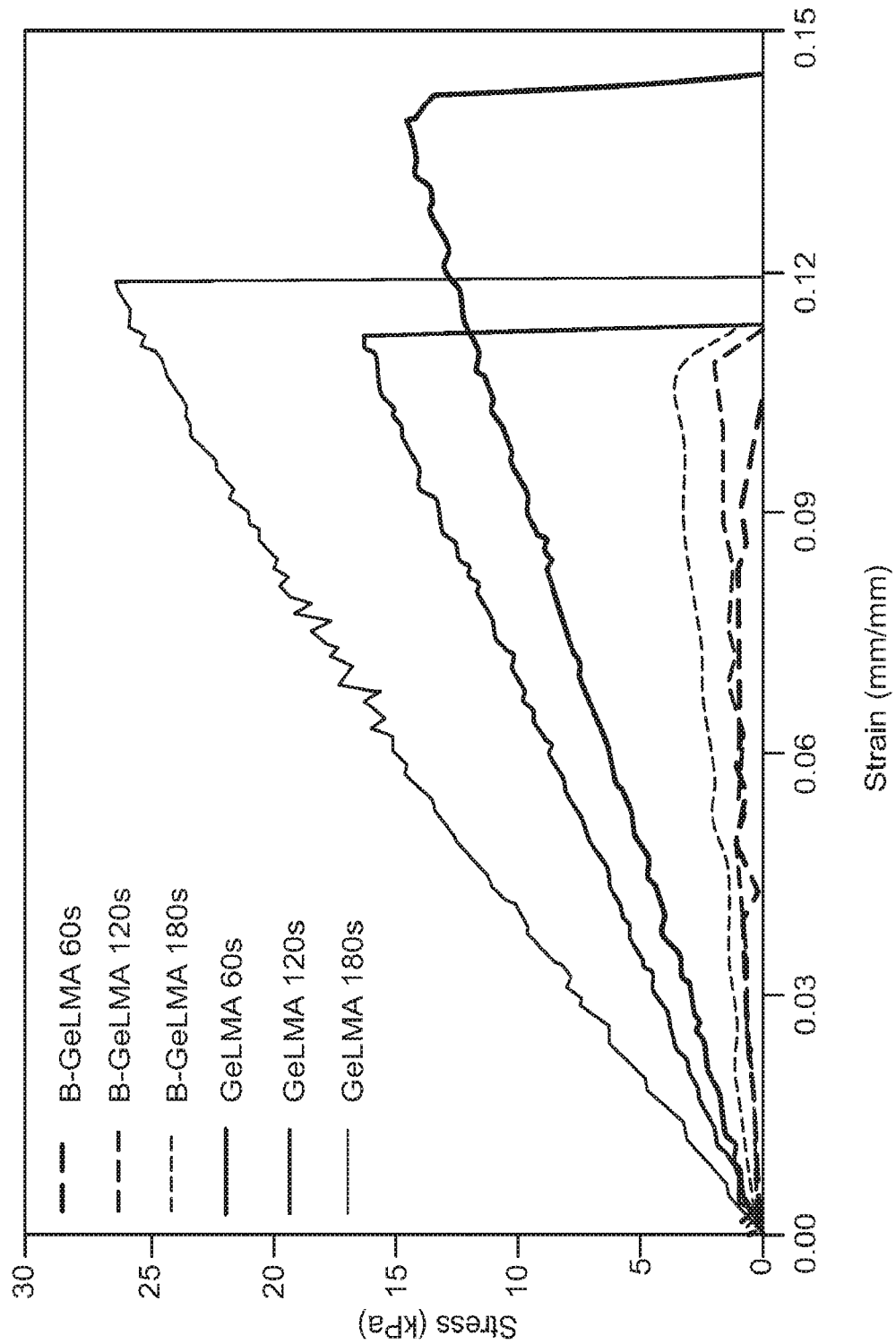
Figure 3D:
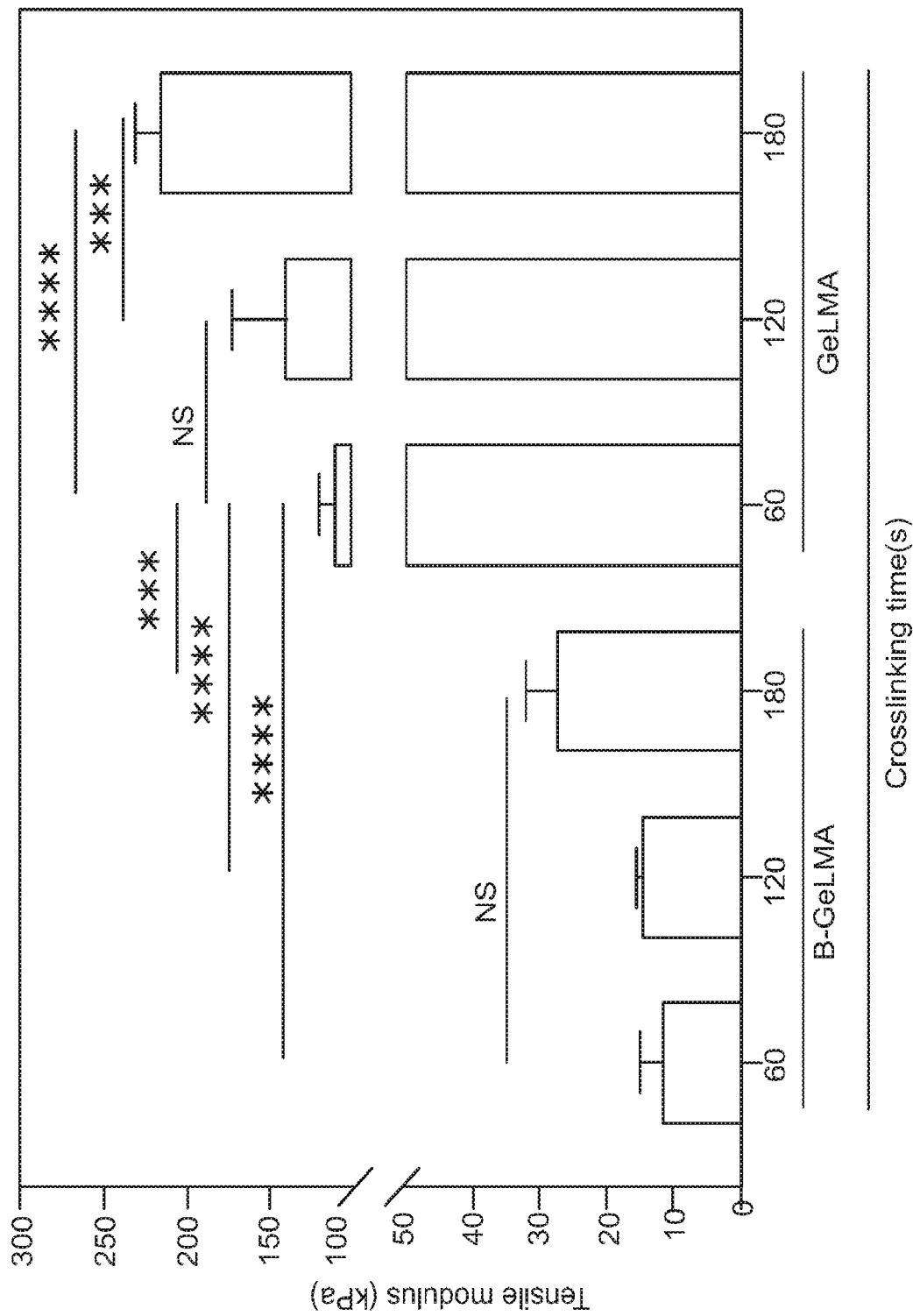

The mechanical properties of B-GelMA are characterized in terms of tensile and compression moduli (FIG. 3b). The high mechanical resilience of B-GelMA scaffolds enables handling them for measuring tensile strength. The tensile stress versus strain for B-GelMA and GelMA scaffolds are presented in FIG. 3c. When prepared similarly, e.g., 2 min of UV light-mediated crosslinking, at a certain strain, the tensile stress of B-GelMA is lower than the bulk material, possibly as a result of high microporosity and lower contact area among beads. FIG. 3d presents the tensile modulus of B-GelMA and bulk scaffolds. B-GelMA attains a tensile modulus in the range of 10-30 kPa, whereas, for the bulk GelMA, the tensile modulus spans ~100-200 kPa, for a crosslinking time ~1-3 min.

Figure 3E:
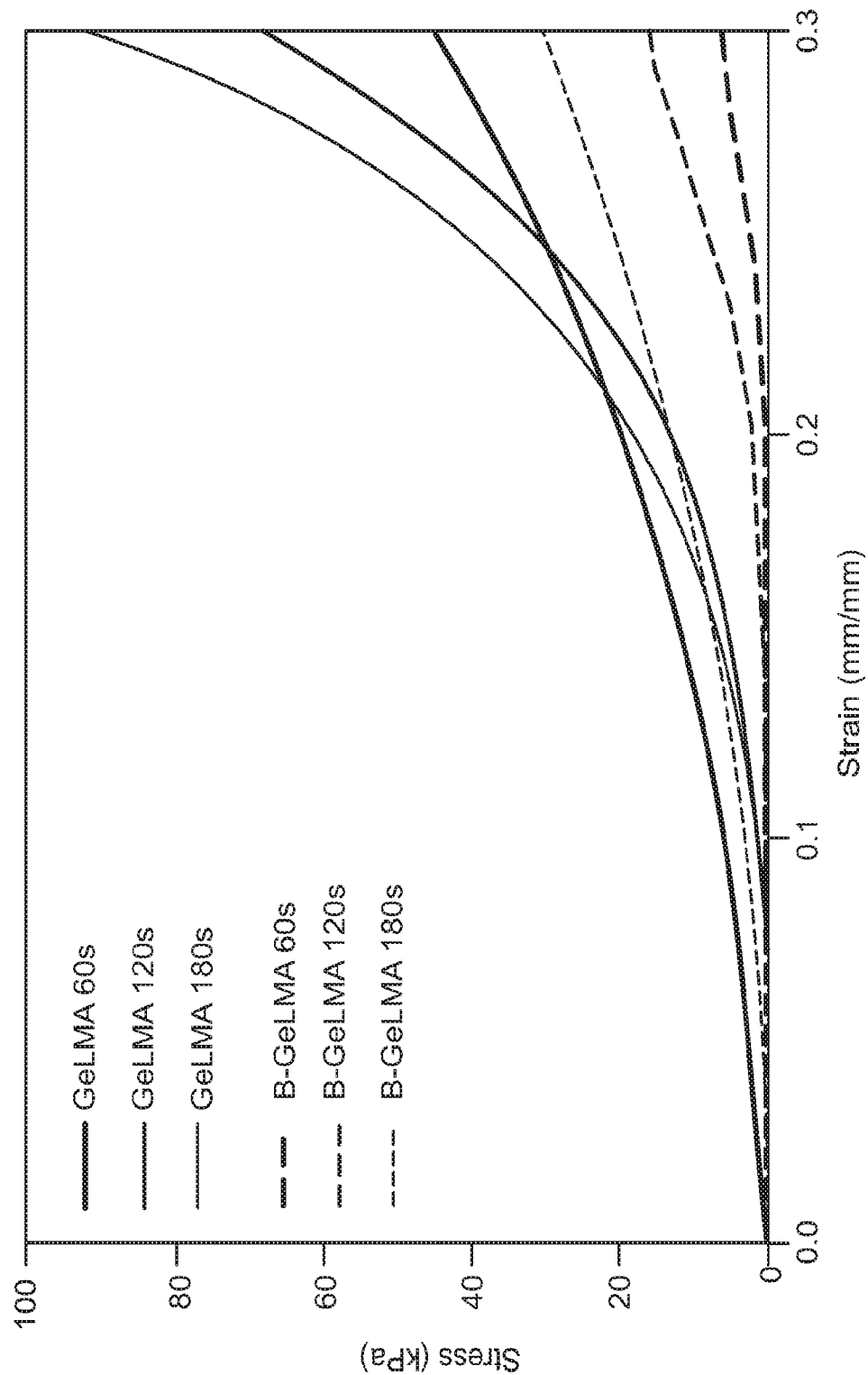
Figure 3F:
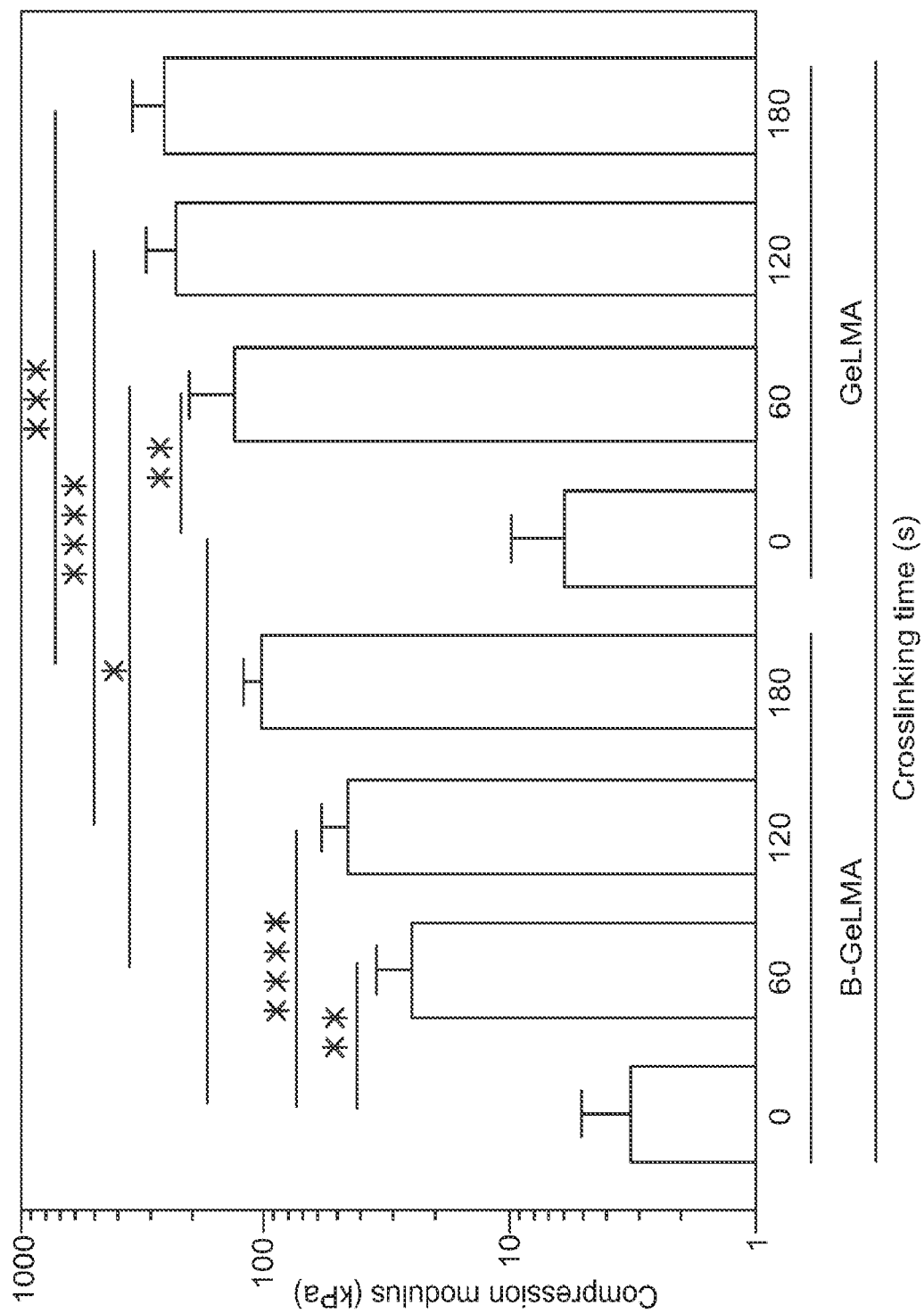

The compression moduli of the scaffolds, measured from the linear fits to the stress-strain curves at strain <10% (FIG. 3e), are summarized in FIG. 3f. When GelMA is not chemically crosslinked, at room temperature, it forms a physical gel with a compression modulus ~3 and 6 kPa for B-GelMA and bulk scaffolds, respectively. Chemical crosslinking for 60, 120, and 180 s results in the formation of mechanically resilient B-GelMA scaffolds with compression moduli ~25, 46, and 107 kPa, respectively. To the best of our knowledge, such a mechanical stiffness is remarkably higher than any other beaded platforms. For example, a maximum compression modulus of ~1 kPa is reported for acrylamide-modified HA doped with SH-containing peptides [25]. In comparison to the bulk GelMA, the compression moduli of B-GelMA scaffolds are lower by 2-5 fold.

Figure 3G:
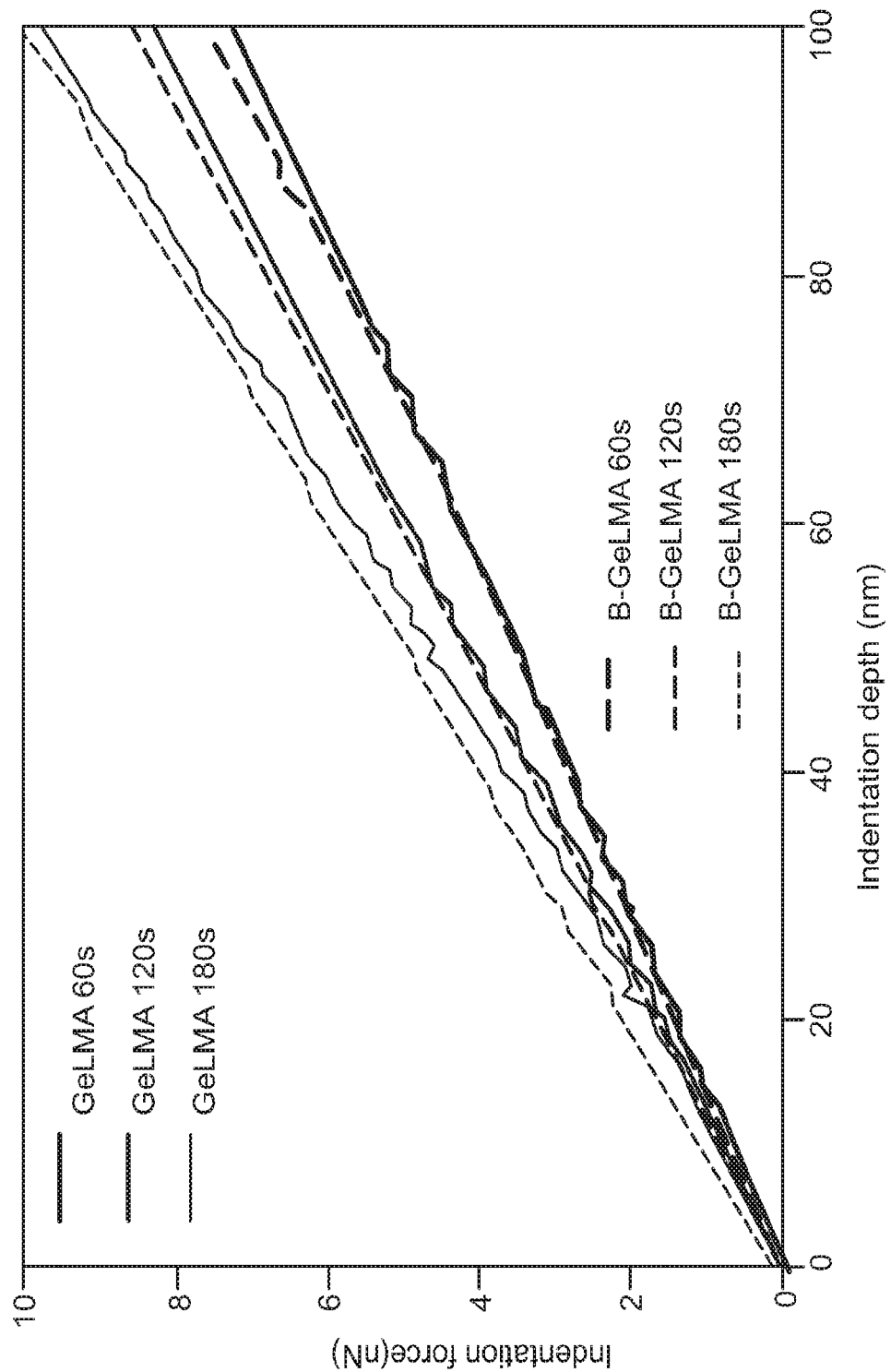
Figure 3H:
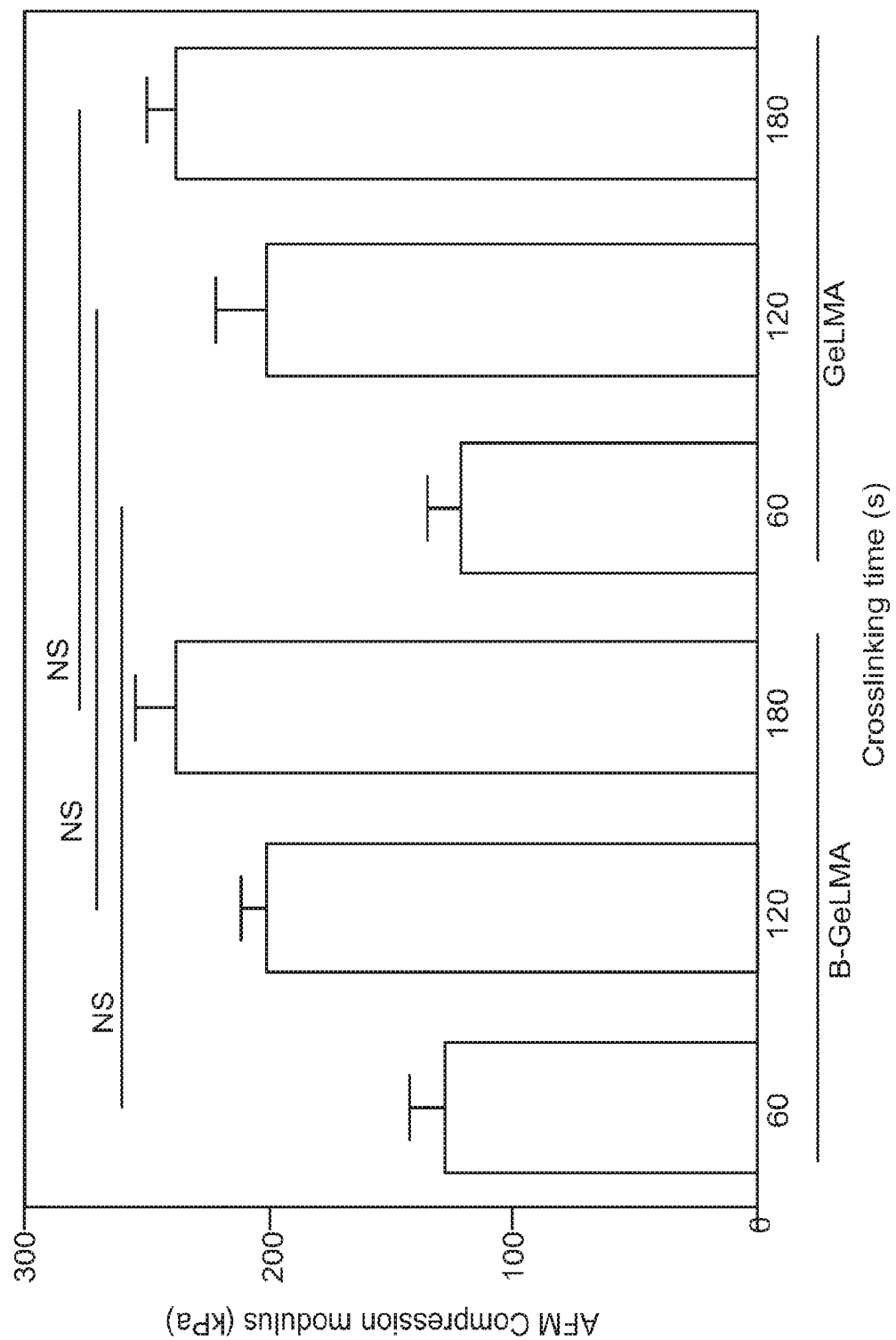
Figure 31:
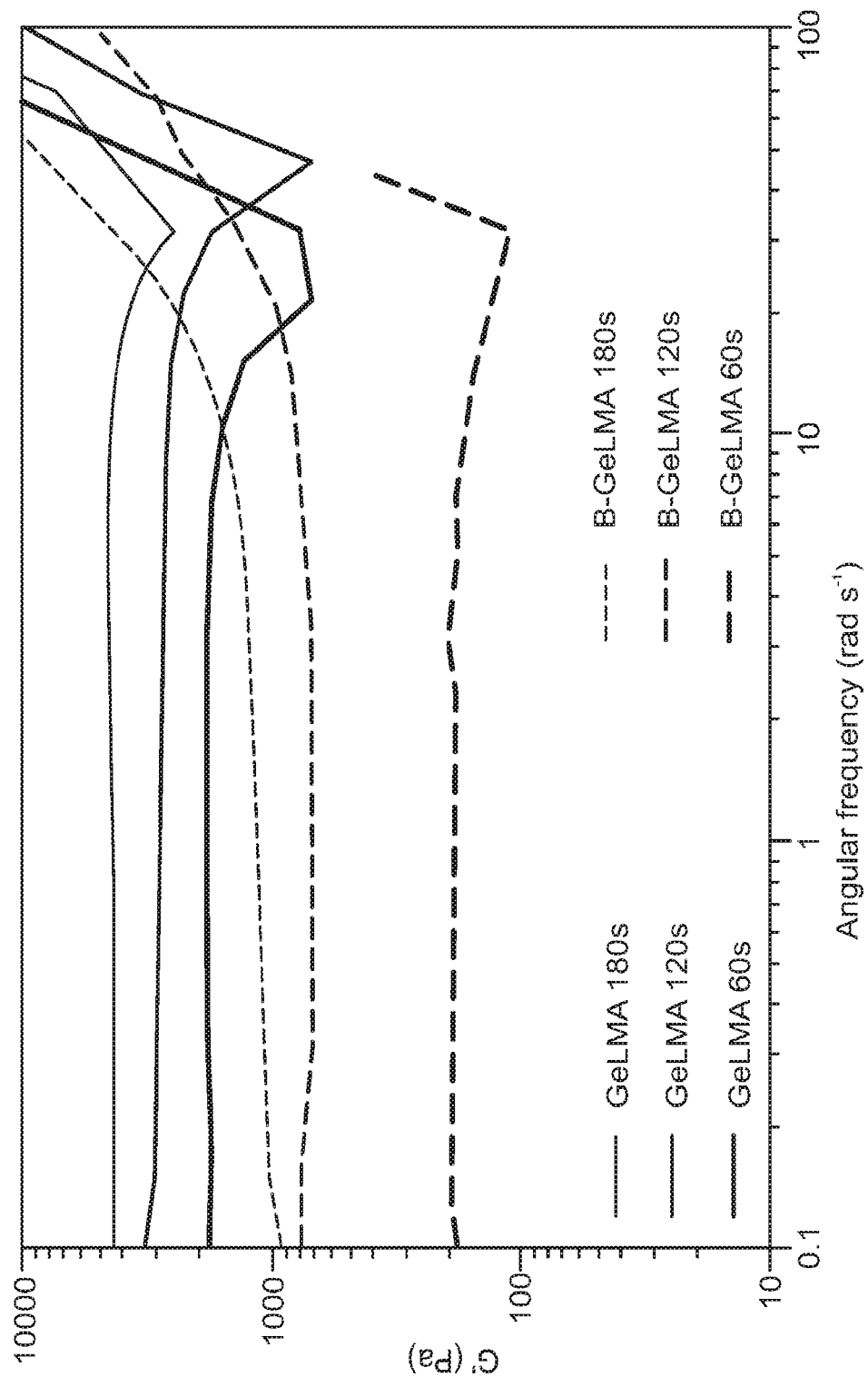

Despite the lower compression modulus of B-GelMA scaffolds than GelMA, we investigated the local stiffness of the single beads in the annealed scaffold using AFM-assisted nanoindentation to identify the stiffness at the microscale relevant to an adhered cell. The compression modulus of the beads was measured at an indentation depth ~100 nm to understand the local stiffness of the scaffolds that cells may experience. FIG. 3g presents the stress-strain curves of B-GelMA and GelMA, obtained through the indentation of the beads and bulk gel. As can be seen in this figure, at a certain strain, the compression stress of beads is close to the bulk hydrogels. The compression moduli of the beads, calculated from a linear fit to the stress-strain curves are very close to the bulk gel (FIG. 3h), attesting to the identical GelMA crosslinking in both types of gels.

Figure 3J:
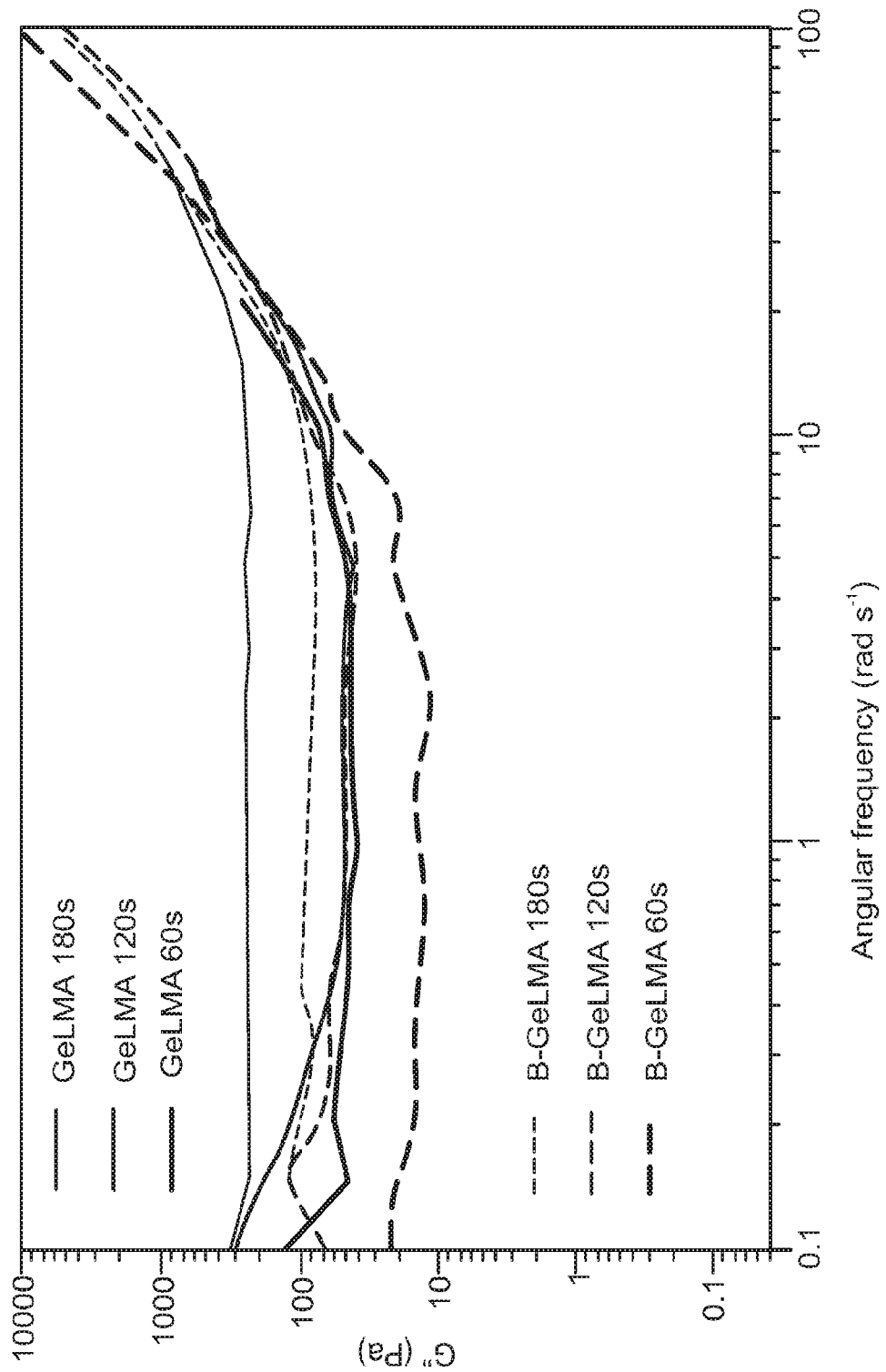
Figure 3K:
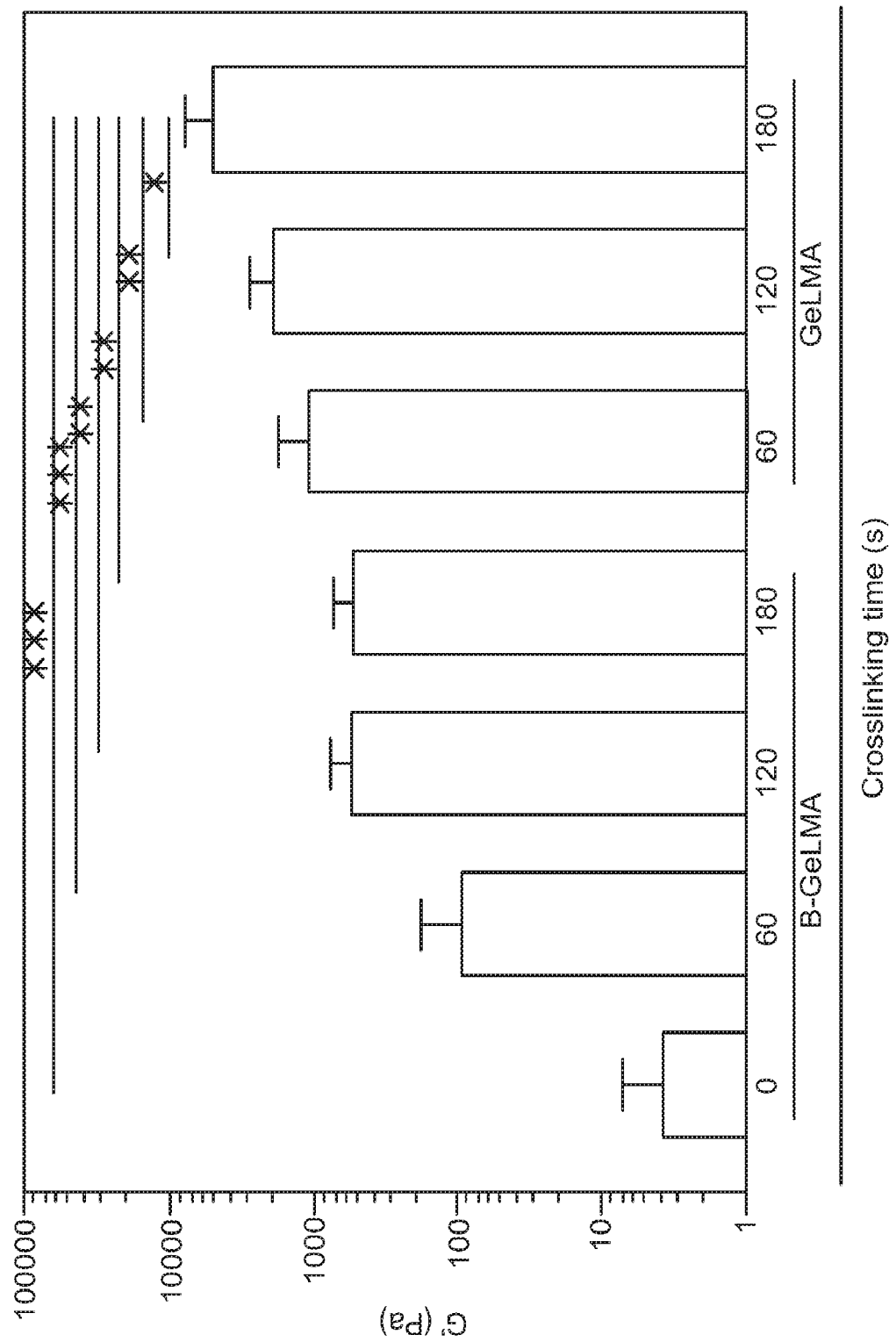
Figure 3L:
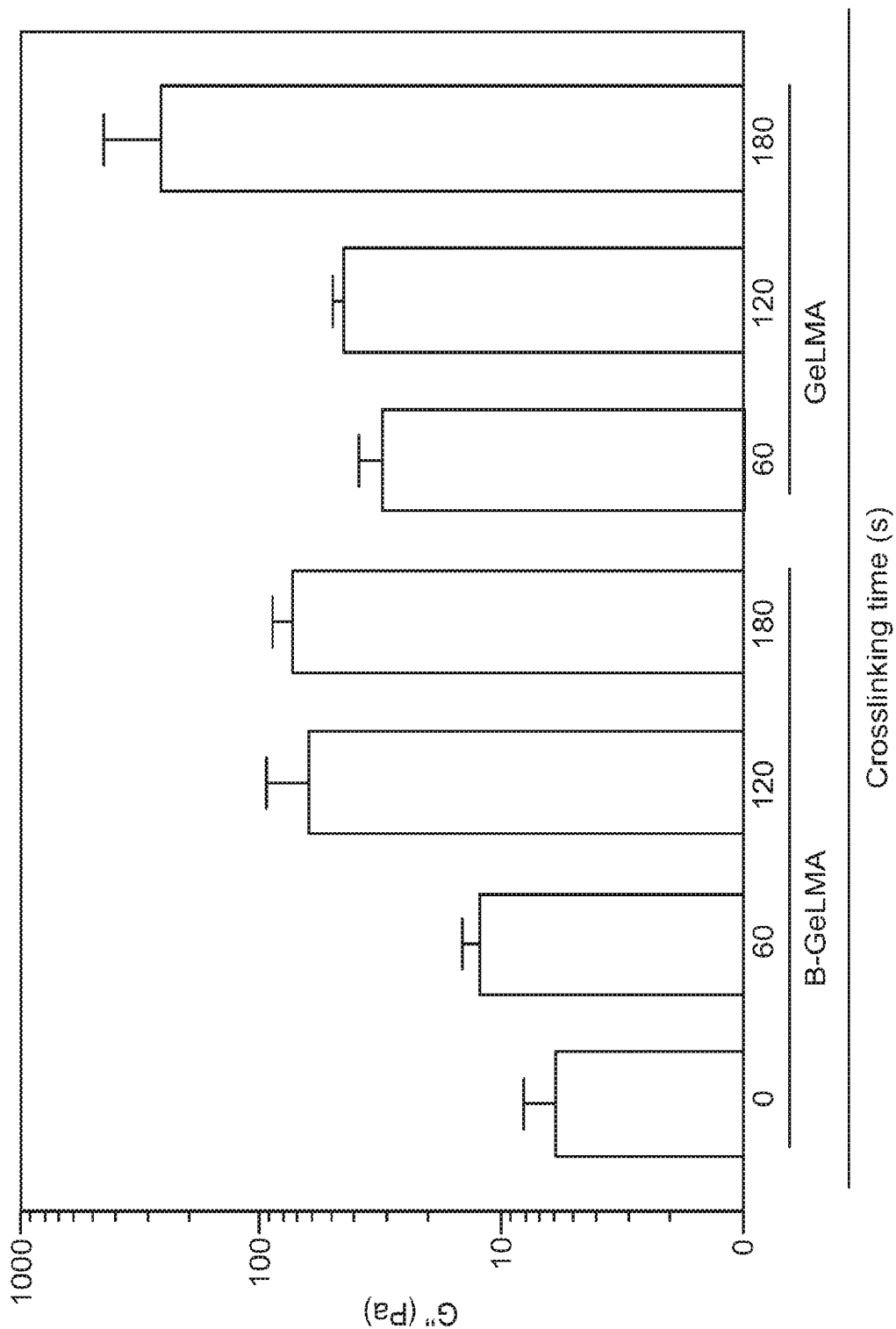

To conduct further structural characterization, the storage G' and loss moduli G" of B-GelMA scaffolds were measured at varying angular frequencies using a standard oscillatory rheology technique. G' and G" versus angular frequency at an oscillatory shear strain ~0.1% are presented in FIGS. 3i and 3j, respectively. At angular frequencies below ~10 rad $s^{-1}$, the storage moduli of the scaffolds are almost independent of the frequency, showing a typical solid-like behavior. Increasing the frequency increases the storage moduli, showing a shift towards a glassy behavior [43]. Accordingly, the B-GelMA scaffolds behave like the bulk GelMA. Increasing the crosslinking time increases the viscoelastic moduli, as observed in the compression and tensile moduli. For example, at an angular frequency ~1 rad $s^{-1}$, the storage moduli ~ order of 100 and ~1000 Pa and loss moduli ~order of 10 and 100 Pa were obtained for B-GelMA with a crosslinking time ~60 and 180 s, respectively. The bulk scaffolds attain higher viscoelastic moduli, e.g., at 180 s crosslinking time, G'~ order of 5000 Pa and G order of 200 Pa, respectively (FIGS. 3k and 3l).

Figure 4:
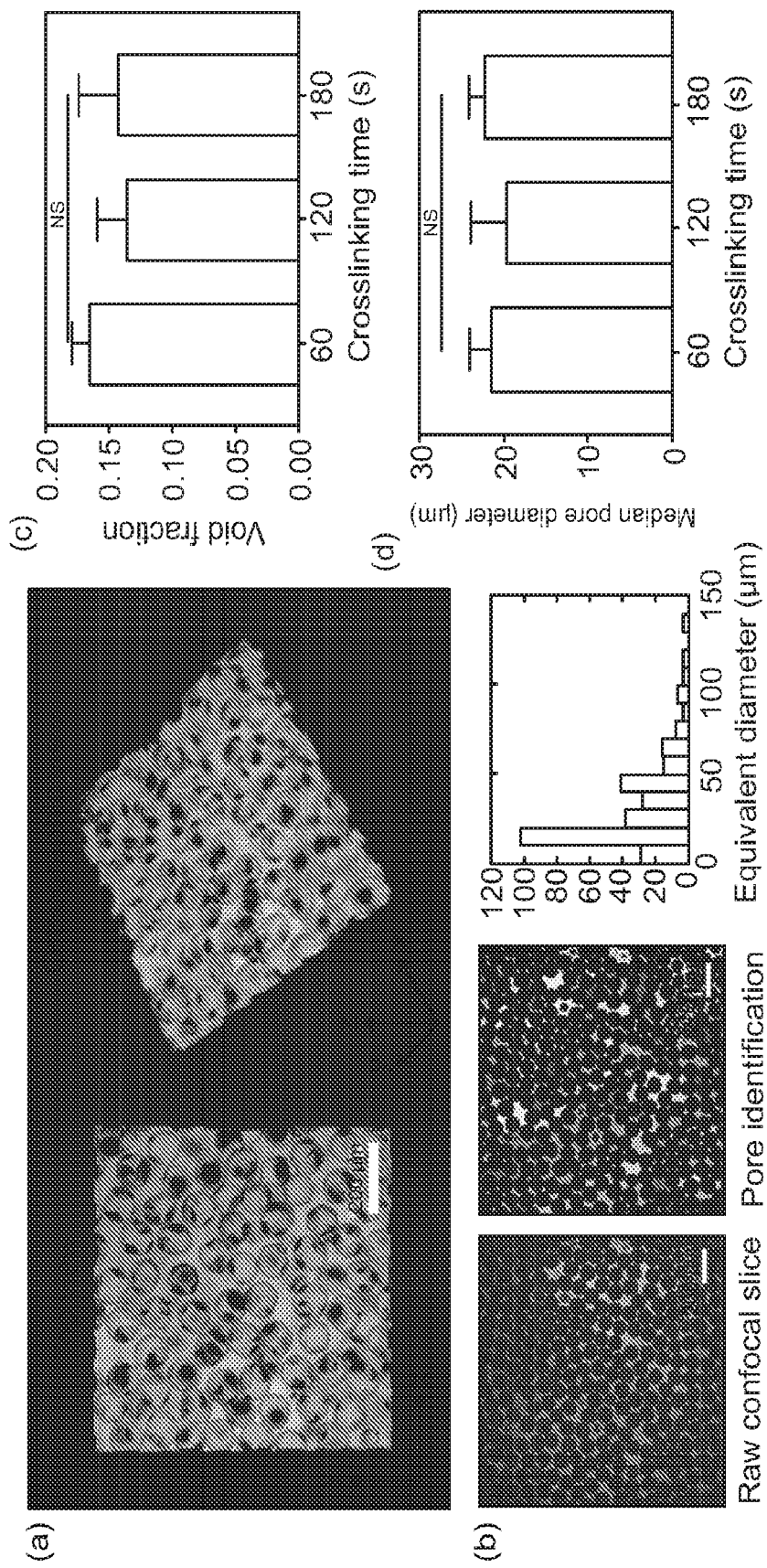
FIGS. 4A-4D. Pore characterization of B-GelMA.

The void fraction of B-GelMA with varying stiffness was measured through the 3D reconstruction of z-stacks, obtained from confocal microscopy of fluorescent-labelled scaffolds. A large molecular weight fluorescent dextran was incubated with the annealed B-GelMA scaffolds, diffusing into the interconnected void spaces without penetrating the beads. FIG. 4a shows the 3D projection of B-GelMA scaffolds from the top and orthographic views, showing the void space, labeled in green. The z-stacks were individually analyzed to measure the diameter distribution of equivalent circles filling the void space (FIG. 4b). The void fraction versus the crosslinking time is presented in FIG. 4c. While increasing the crosslinking time increases the scaffold stiffness (FIG. 3), it does not have any significant effect on the void fraction, which is ~15% for all scaffolds. The median pore diameter, presented in FIG. 4d, has a similar trend to void fraction. Increasing the B-GelMA scaffold stiffness does not affect the pore size, and all the scaffolds attain a median pore diameter ~ 20 µm. Accordingly, B-GelMA generates a protein-based bottom-up hydrogel scaffold with orthogonal porosity and stiffness.

Figure 5A:
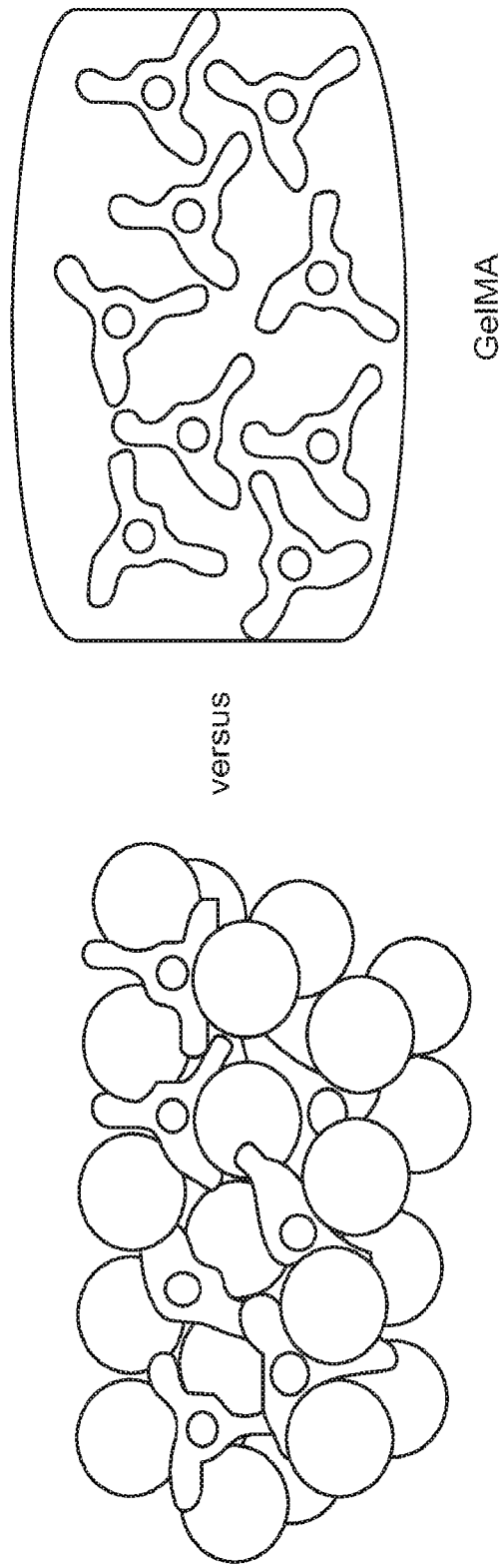

The biological activity of B-GelMA in hosting cells was investigated by mixing NIH/3T3 fibroblasts with physically-crosslinked GelMA beads, followed by UV light exposure for 120 s to form cell-laden B-GelMA scaffolds. A high concentration of GelMA (20% w/v) was selected to elucidate the fundamental differences between the bead-based and the bulk scaffolds. The fibroblasts were cultured for 14 days in the B-GelMA scaffolds. FIG. 5a presents the live/dead assay of cell-laden B-GelMA during a 2-week culture period. While cells readily integrate in the B-GelMA scaffolds through filling the interconnected microscale voids and adhere to the beads, permitting their spreading and proliferation in the complete course of culture (FIG. 5b), the majority of encapsulated cells in the bulk GelMA do not survive the first day of culture (FIG. 5c). Enhanced cell spreading on and among the beads in B-GelMA is presented in FIG. 5d. The cell viability was quantified by normalizing the number of live cells with the total cell number, presented in FIG. 5e. The B-GelMA scaffold affords ~100% cell viability; whereas, the cell viability on the bulk GelMA ~0%. The metabolic activity of the cells, encapsulated in the scaffolds, measured using the PrestoBlue® assay (FIG. 5f), demonstrate ~3.4, 8.5, 17.9, and 25.8 folds increase in days 3, 5, 7, and 14 post seeding, respectively, attesting to the enhanced proliferation.

Cell seeding from the scaffold surface inward was studied by placing a droplet of HUVECs (~5×$10^4$ cells) on the annealed/crosslinked scaffolds, presented schematically in FIG. 6a. The droplet was allowed to be uptaken by the scaffold for ~5 min, followed by 3D confocal imaging. FIG. 6b presents the 3D projection of B-GelMA and GelMA scaffolds from side and orthographic views. As can be seen in these images, immediate 3D cell seeding, i.e., penetration inside the B-GelMA takes place; whereas, the bulk GelMA scaffolds do not permit cell penetration. The fast penetration of cells inside the B-GelMA scaffolds may be a result of capillary forces among the beads, enhancing cell transportation via convection. Such enhanced delivery within a scaffold enabled by the interconnected microporosity may enable the rapid infiltration of cells inside B-GelMA, as universal scaffolds for advanced applications, such as time-sensitive cell culture (e.g., neonatal cardiomyocyte for cell therapy post myocardial infarction) and a broad range of co-culture systems, including the vascularization of bone and tumor models.

Regulating cellular behavior and function using chemical and biological cues of naturally-derived materials demands fine tuning of their mechanical and structural properties. Incorporating cells in chemically-modified bulk 3D hydrogel scaffolds permits improved cell-cell and cell-matrix interactions in a microenvironment that mimics ECM. However, bulk hydrogels with high stiffness and small pore size are detrimental to cells, preventing inward oxygen and nutrient diffusion and cell-matrix migration, proliferation and integration. We have introduced a novel hydrogel platform based on annealing tens of micrometer-sized beads made up of a chemically-modified naturally-derived protein, GelMA, readily allowing for orthogonal physical and chemical dual crosslinking. Temperature-driven physical crosslinking of the beads enables the facile purification of gel building blocks without further chemical reaction, overcoming some of the challenges of newly-emerging beaded scaffolds, including oxygen-mediated impaired crosslinking. Beaded GelMA (B-GelMA) provides remarkable cell viability, adhesion, proliferation, and immediate 3D seeding, which would otherwise be impossible at a high concentration of bulk GelMA. This technology may be extended to other heat-responsive materials, setting the stage for transforming bulk to beaded scaffolds with independent control of microporosity from stiffness through a facile microfluidic strategy.

The following references are those noted in the disclosure above.

REFERENCES

[1] N. A. Peppas, J. Z. Hilt, A. Khademhosseini, R. Langer, Hydrogels in biology and medicine: from molecular principles to bionanotechnology, Adv. Mater. 18 (2006) 1345-1360.

[2] J. L. Drury, D. J. Mooney, Hydrogels for tissue engineering: scaffold design variables and applications, Biomaterials. 24 (2003) 4337-4351.

[3] E. Caló, V. V Khutoryanskiy, Biomedical applications of hydrogels: A review of patents and commercial products, Eur. Polym. J. 65 (2015) 252-267.

[4] K. H. Bouhadir, K. Y. Lee, E. Alsberg, K. L. Damm, K. W. Anderson, D. J. Mooney, Degradation of partially oxidized alginate and its potential application for tissue engineering, Biotechnol. Prog. 17 (2001) 945-950. doi: 10.1021/bp010070p.

[5] A. S. Hoffman, Hydrogels for biomedical applications, Adv. Drug Deliv. Rev. 64 (2012) 18-23.

[6] J. Leijten, J. Seo, K. Yue, G. Trujillo-de Santiago, A. Tamayol, G. U. Ruiz-Esparza, S. R. Shin, R. Sharifi, I. Noshadi, M. M. Alvarez, Spatially and temporally controlled hydrogels for tissue engineering, Mater. Sci. Eng. R Reports. 119 (2017) 1-35.

[7] J. Yang, Y. S. Zhang, K. Yue, A. Khademhosseini, Cell-laden hydrogels for osteochondral and cartilage tissue engineering, Acta Biomater. 57 (2017) 1-25.

[8] Y. S. Zhang, A. Khademhosseini, Advances in engineering hydrogels, Science (80-.). 356 (2017) eaaf3627.

[9] H. W. Ooi, S. Hafeez, C. A. van Blitterswijk, L. Moroni, M. B. Baker, Hydrogels that listen to cells: a review of cell-responsive strategies in biomaterial design for tissue regeneration, Mater. Horizons. 4 (2017) 1020-1040.

[10] T. E. Brown, K. S. Anseth, Spatiotemporal hydrogel biomaterials for regenerative medicine. Chem. Soc. Rev. 46 (2017) 6532-6552.

[11] W. Lu, X. Le, J. Zhang, Y. Huang, T. Chen, Supramolecular shape memory hydrogels: a new bridge between stimuli-responsive polymers and supramolecular chemistry, Chem. Soc. Rev. 46 (2017) 1284-1294.

[12] R. Y. Tam, L. J. Smith, M. S. Shoichet, Engineering cellular microenvironments with photo-and enzymatically responsive hydrogels: Toward biomimetic 3D cell culture models, Acc. Chem. Res. 50 (2017) 703-713.

[13] Y. Lu, A. A. Aimetti, R. Langer, Z. Gu, Bioresponsive materials, Nat. Rev. Mater. 2 (2017) 16075.

[14] H. Nakamura, A. A. Lee, A. S. Afshar, S. Watanabe. E. Rho, S. Razavi, A. Suarez, Y.-C. Lin, M. Tanigawa, B. Huang, Intracellular production of hydrogels and synthetic RNA granules by multivalent molecular interactions, Nat. Mater. 17 (2018) 79.

[15] T. L. Sun, T. Kurokawa, S. Kuroda, A. Bin Ihsan, T. Akasaki, K. Sato, M. A. Haque, T. Nakajima, J. P. Gong, Physical hydrogels composed of polyampholytes demonstrate high toughness and viscoelasticity, Nat. Mater. 12 (2013) 932.

[16] A. M. Rosales, K. S. Anseth, The design of reversible hydrogels to capture extracellular matrix dynamics, Nat. Rev. Mater. 1 (2016) 15012.

[17] A. Khademhosseini, R. Langer, Microenginecred hydrogels for tissue engineering, Biomaterials. 28 (2007) 5087-5092.

[18] B. G. Chung, K.-H. Lee, A. Khademhosseini, S.-H. Lee, Microfluidic fabrication of microengineered hydrogels and their application in tissue engineering, Lab Chip. 12 (2012) 45-59.

[19] N. Annabi, J. W. Nichol, X. Zhong, C. Ji, S. Koshy, A. Khademhosseini, F. Dehghani, Controlling the porosity and microarchitecture of hydrogels for tissue engineering, Tissue Eng. Part B Rev. 16 (2010) 371-383.

[20] J. W. Nichol, S. T. Koshy, H. Bae, C. M. Hwang, S. Yamanlar, A. Khademhosseini, Cell-laden microengineered gelatin methacrylate hydrogels. Biomaterials. 31 (2010) 5536-5544.

[21] H. Aubin, J. W. Nichol, C. B. Hutson, H. Bae, A. L. Sieminski, D. M. Cropek, P. Akhyari, A. Khademhosseini, Directed 3D cell alignment and elongation in microengineered hydrogels, Biomaterials. 31 (2010) 6941-6951.

[22] P.-G. De Gennes, P.-G. Gennes, Scaling concepts in polymer physics, Cornell university press, 1979.

[23] W. Li, L. Zhang, X. Ge, B. Xu, W. Zhang, L. Qu, C.-H. Choi, J. Xu, A. Zhang, H. Lee, Microfluidic fabrication of microparticles for biomedical applications, Chem. Soc. Rev. 47 (2018) 5646-5683.

[24] D. R. Griffin, W. M. Weaver, P. O. Scumpia. D. Di Carlo, T. Segura, Accelerated wound healing by injectable microporous gel scaffolds assembled from annealed building blocks, Nat. Mater. 14 (2015) 737-744. doi:10.1038/nmat4294.

[25] E. Sideris, D. R. Griffin, Y. Ding, S. Li, W. M. Weaver, D. Di Carlo, T. Hsiai, T. Segura, Particle Hydrogels Based on Hyaluronic Acid Building Blocks, ACS Biomater. Sci. Eng. 2 (2016) 2034-2041. doi: 10.1021/acsbiomaterials.6b00444.

[26] J. E. Mealy, J. J. Chung, H. H. Jeong, D. Issadore, D. Lee, P. Atluri, J. A. Burdick, Injectable Granular Hydrogels with Multifunctional Properties for Biomedical Applications, Adv. Mater. 30 (2018) 1-7. doi: 10.1002/adma.201705912.

[27] K. Krutkramelis, B. Xia, J. Oakey, Monodisperse polyethylene glycol diacrylate hydrogel microsphere formation by oxygen-controlled photopolymerization in a microfluidic device, Lab Chip. 16 (2016) 1457-1465.

[28] M. E. Hoque, T. Nuge, T. K. Yeow, N. Nordin, R. Prasad, Gelatin based scaffolds for tissue engineering-a review. Polym. Res. J. 9 (2015) 15.

[29] M. Santoro, A. M. Tatara, A. G. Mikos, Gelatin carriers for drug and cell delivery in tissue engineering, J. Control. Release. 190 (2014) 210-218.

[30] J. B. Rose, S. Pacelli, A. J. El Haj, H. S. Dua. A. Hopkinson, L. J. White, F. R. A. J. Rose, Gelatin-based materials in ocular tissue engineering, Materials (Basel). 7 (2014) 3106-3135.

[31] S. Gnavi, L. Di Blasio, C. Tonda-Turo, A. Mancardi, L. Primo, G. Ciardelli, G. Gambarotta, S. Geuna, I. Perroteau, Gelatin-based hydrogel for vascular endothelial growth factor release in peripheral nerve tissue engineering, J. Tissue Eng. Regen. Med. 11 (2017) 459-470.

[32] S. Pina, J. M. Oliveira, R. L. Reis, Natural-based nanocomposites for bone tissue engineering and regenerative medicine: A review, Adv. Mater. 27 (2015) 1143-1169.

[33] K. Yue, G. T. Santiago, M. M. Alvarez, A. Tamayol, N. Annabi, A. Khademhosseini, Synthesis, properties, and biomedical applications of gelatin methacryloyl (GelMA) hydrogels, Biomaterials. 73 (2015) 254-271. doi:10.1016/j.biomaterials.2015.08.045.

[34] K. Yue, X. Li, K. Schrobback, A. Sheikhi, N. Annabi, J. Leijten, W. Zhang, Y. S. Zhang, D. W. Hutmacher, T. J. Klein, A. Khademhosseini, Structural analysis of photocrosslinkable methacryloyl-modified protein derivatives, Biomaterials. 139 (2017) 163-171. doi: 10.1016/j.biomaterials.2017.04.050.

[35] X. Zhao, Q. Lang, L. Yildirimer, Z. Y. Lin, W. Cui, N. Annabi, K. W. Ng, M. R. Dokmeci, A. M. Ghaemmaghami, A. Khademhosseini, Photocrosslinkable gelatin hydrogel for epidermal tissue engineering. Adv. Healthc. Mater. 5 (2016) 108-118.

[36] B. J. Klotz, D. Gawlitta. A. J. W. P. Rosenberg, J. Malda. F. P. W. Melchels, Gelatin-methacryloyl hydrogels: towards biofabrication-based tissue repair, Trends Biotechnol. 34 (2016) 394-407.

[37] A. Sheikhi, J. de Rutte, R. Haghniaz, O. Akouissi, A. Sohrabi, D. Di Carlo, A. Khademhosseini. Modular hydrogels from macromolecules with orthogonal thenmo-chemical responsivity: Microfluidic fabrication and characterization, MethodsX. Submitted (2018).

[38] A. E. Danks, S. R. Hall, Z. Schnepp, The evolution of 'sol-gel'chemistry as a technique for materials synthesis, Mater. Horizons. 3 (2016) 91-112.

[39] G. Ninan, J. Joseph, Z. A. Aliyamvettil, A comparative study on the physical, chemical and functional properties of carp skin and mammalian gelatins, J. Food Sci. Technol. 51 (2014) 2085-2091.

[40] Q.-Z. Chen, A. Bismarck. U. Hansen. S. Junaid, M. Q. Tran. S. E. Harding, N. N. Ali, A. R. Boccaccini, Characterisation of a soft elastomer poly(glycerol sebacate) designed to match the mechanical properties of myocardial tissue, Biomaterials. 29 (2008) 47-57. doi: https://doi.org/10.1016/j.biomaterials.2007.09.010.

[41] N. J. Kaiser, K. L. K. Coulombe, Physiologically inspired cardiac scaffolds for tailored in vivo function and heart regeneration, Biomed. Mater. 10 (2015) 34003.

[42] J. M. Shaw, N. M. Hamad, T. J. Coleman, M. J. Egger, Y. Hsu, R. Hitchcock, I. E. Nygaard, Intra-abdominal pressures during activity in women using an intra-vaginal pressure transducer, J. Sports Sci. 32 (2014) 1176-1185.

[43] J. M. Zuidema, C. J. Rivet, R. J. Gilbert, F. A. Morrison, A protocol for rheological characterization of hydrogels for tissue engineering strategies, J. Biomed. Mater. Res. Part B Appl. Biomater. 102 (2014) 1063-1073.

Illustrative Methods and Materials Useful with Embodiments of the Invention

Silicon wafers (University Wafer, MA, USA), negative photoresist (KMPR 1050, MicroChem Corp., MA, USA), and polydimethylsiloxane (PDMS) base and the curing agent (SYLGARD™ 184 Elastomer Kit, Dow Corning, MI, USA) were used to construct the microfluidic chips. Tygon Flexible Plastic Tubing 0.02" ID×0.06" OD (Saint-Gobain PPL Corp., CA, USA) and 1569-PEEK Tubing Orange 1/32" OD×0.020" ID (IDEX Corp., IL, USA) were used with the microfluidic device. Aquapel® Glass Treatment was purchased from Pittsburgh Glass Works LLC (PA, USA). 3M™ Novec™ 7500 Engineered Fluid (Novec 7500 oil) was provided by 3M (MN, USA). Type-A gelatin from porcine skin (300 bloom), methacrylic anhydride (MA, 94%), photoinitiator 2-hydroxy-1-(4-(hydroxyethoxy)phenyl)-2-methyl-1-propanone (Irgacure 2959), 1H,1H,2H,2H-Perfluoro-1-octanol 97%, and fluorescein isothiocyanate-dextran solution (500 kDa) were purchased from Sigma-Aldrich (MO, USA). Dialysis membrane with 12-14 kDa molecular weight cutoff (MWCO) was provided by Spectrum Lab Inc (CA, USA). Microscope glass cover slides (25 mm 75 mm×1 mm) were from Fisher Scientific (PA, USA), and cover slips (No. 1) were from VWR (PA, USA). Milli-Q water with an electrical resistivity ~18.2 MΩ cm at 25° C. was provided by Millipore Corporation. Pico-Surf™ 1 (5% (w/w) in Novec™ 7500) was purchased from Sphere Fluidics Inc (Cambridge, UK). Biopsy punch (diameter ~8 mm) was from Integra Miltex (NJ, USA). Cyanoacrylate-based adhesive was Krazy glue (Elmer's Products, NC, USA). Cell-Tak tissue adhesive (Corning, NY, USA), AFM probe (spring constant ~0.01 N m-1) with an affixed polystyrene bead (diameter ~2.5 sm), mounted on a silicon nitride (SN) cantilever (Novascan, Iowa, USA) were used for AFM indentation experiments. NIH/3T3 fibroblast cells and human umbilical vein endothelial cells (HUVECs) were purchased from the American Type Culture Collection (ATCC, VA, USA). Fetal bovine serum (FBS), penicillin/streptomycin (P/S), Dulbecco's modified Eagle medium (DMEM), Dulbecco's phosphate-buffered saline (DPBS) solution (1×) and powder, trypsin-ethylenediaminetetraacetic acid (EDTA) (0.5%, 10×), and Hank's Balanced Salt Solution (HBSS, 1×) were provided by Gibco (NY, USA). Endothelial cell growth medium 2 and Supplement-Mix were from PromoCell (Heidelberg, Germany). Presto-Blue™ cell viability reagent and LIVE/DEAD™ viability/cytotoxicity kit were from Invitrogen by ThermoFisher Scientific (OR, USA). Cell culture flasks (75 cm2, Corning, NY, USA) and polystyrene 6-well tissue culture-treated plates (Falcon, NC, USA) were used to culture cells.

Methods

Fabrication of the Microfluidic Device

We have modified a microfluidic water-in-oil emulsion method [1-3] to fabricate uniform-sized microbeads [4]. A flow-focus device was fabricated using soft lithography. Briefly, 4 inch mechanical grade silicon wafers were coated with 80 and 70 µm layers of negative photoresist (KMPR 1050) and patterned in sequence using standard photolithography techniques. PDMS base and the curing agent were mixed at a ratio of 10 to 1, poured onto the molds in petri dishes, degassed, and cured in an oven at 65° C. for >4 h. The PDMS device was peeled from the mold and punched with 0.8 mm holes at the inlets and outlets. Devices and glass slides were then activated via air plasma (Plasma Cleaner, Harrick Plasma, NY, USA) and bonded together to enclose the microchannels. The devices were then treated with Aquapel and subsequently washed with Novec 7500 oil to make channel surfaces fluorophilic.

GelMA Synthesis

GelMA with a high degree of methacryloyl substitution was synthesized according to our previous publications [5,6]. Briefly, DPBS (100 mL) was heated to 50° C. to dissolve the gelatin (10 g). While stirring at 240 rpm, MA (8 mL) was added to the gelatin solution dropwise, resulting in a turbid mixture, which was stirred for 2 h at 50° C. This condition has been particularly chosen to prevent the hydrolysis of protein [6,7]. To stop the reaction, excessive DPBS was added to the reaction mixture, followed by dialysis using 12-14 kDa molecular weight cutoff (MWCO) membranes for at least seven days at 40° C. to remove methacrylic acid and other impurities. A clear solution was obtained after dialysis, which was lyophilized to yield white solid GelMA.

Bulk GelMA Fabrication

Freeze-dried GelMA was dissolved in DPBS, containing the photoinitiator (Irgacure 2959, 0.5% w/v) at 80° C. The crosslinking setup consisted of a microscope glass cover slide with two stacks of cover slips on both sides to set the sample thickness ~ 0.3-1 mm, length ~25 mm, and width ~10-20 mm. A desired amount of the solution was pipetted in the gap between the cover slips and covered with a cover slip, followed by UV light (360480 nm) exposure at an intensity ~10 mW $cm^{-2}$ (Omnicure, Excelitas, CA, USA) for 1, 2, or 3 min to yield bulk gels from which small samples were cut (for tensile tests) or punched (for compression experiments). Other samples were prepared similarly in smaller sizes for cell culture using the cover glasses and spacers.

GelMA Bead Fabrication

GelMA was dissolved in a desired medium, such as DPBS, including the photoinitiator (0.5% w/v, Irgacure 2959) to afford GelMA solutions upon heating at 80° C. for at least 20 min. These solutions were used as the aqueous, dispersed phase in the microfluidic device along with the pinching flows of Novec 7500 oil-surfactant (0.5 wt % PicoSurf) mixture, injected into the flow-focusing device using syringe pumps (Harvard Apparatus PHD 2000, MA, USA) to form surfactant-stabilized tens of micron-sized beads of GelMA in the oil (continuous) phase. The syringe and tubing were maintained at 37-40° C. to prevent sol-gel transition and device blockage. The bead suspension in oil was collected in a microcentrifuge tube and stored at 4° C. overnight.

Fabrication of Beaded GelMA (B-GelMA) Scaffolds

To prepare the microbeads for annealing, excess oil was removed from the suspension through pipetting, and a 20% perfluorooctanol solution in Novec 7500 oil was added to the bead suspension (1:1 volume ratio) to break down the emulsion and remove the surfactant at 4° C. DPBS solution (4° C.) including the photoinitiator (0.5% (w/v) Irgacure 2959) was added to the suspension for dilution, and the microbeads were transferred to a separate container via pipetting. The suspension was pulse centrifuged (6300 rpm, 10 s, GmCLab mini centrifuge, Gilson, France) to pack the microbeads, followed by removing the supernatant. The sample temperature was always maintained at 4° C. using a cold-water bath. The concentrated microbead suspension was then pipetted on a microscope glass slide using a positive displacement pipette (MICROMAN® E, Gilson, WI, USA), and sandwiched similar to the bulk gels, followed by UV light exposure at an intensity ~10 mW $cm^{+2}$ for 1, 2, or 3 min, resulting in the chemical crosslinking of microbeads in situ as well as annealing of microbeads to neighboring beads in physical contact. Importantly, the crosslinking and annealing reactions occur simultaneously and prior to the melting of the physically gelled GelMA beads, enabling the maintenance of an interconnected microporous structure in the gaps between neighboring beads. The temperature of a delivery site combined with the time between delivery and light-based crosslinking can be used to tune the level of microporosity in some embodiments. For example, the delivery site can be maintained at 4-10° C. to prevent significant melting of the GelMA beads prior to crosslinking, thus maintaining the largest pore sizes. A higher temperature (e.g. 10-20° C.) and/or longer time (>5 min) between delivery and crosslinking can be used to reduce the pore size between the GelMA beads as they partially melt prior to crosslinking and annealing.

Pore Size Measurement

Samples were prepared as previously described using 20% (w/v) GelMA beads exposed to 10 mW $cm^{-2}$ UV light for 1, 2, and 3 min. Scaffolds were incubated in a fluorescein isothiocyanate-dextran solution (15 mM) to visualize the void space in the scaffolds. Confocal images of the scaffolds were taken using a Leica inverted SP5 confocal microscope (Germany) at the California NanoSystems Institute (CNSI). For each sample (3 per condition), 77 z-slices were captured, spanning a total distance of 100 µm. Void fraction and pore diameter were analyzed using a custom-developed Matlab code (Matlab, version 2016b). Briefly, adaptive thresholding was used to convert stacked images into discrete regions, and void fraction was calculated based on voxel volume of void space regions. Average pore diameter was calculated as previously described [8].

Mechanical Analyses

For compression tests, GelMA samples were exposed to 10 mW $cm^{-2}$ UV light for 1, 2, or 3 min. punched in disks with diameter ~8 mm and height ~1 mm. The gels were removed from the cover glass and incubated in DPBS for 1 h at room temperature. Compression tests were conducted using an Instron mechanical tester (Instron 5542, Norwood, Mass., USA) at a rate ~ 1 mm $min^{-1}$. The best fit to the linear stress-strain region at 0-10% strain was used to calculate the compression modulus (stress/strain). For tensile tests, crosslinked samples were cut (10 mm×15 mm×1 mm), glued to two pieces of paper from each end using Krazy glue and transferred to the Instron tensile test grips to perform the experiment at a rate ~10 mm min$^{-1}$. The slope of linear stress-strain region at strain <10% provided the tensile modulus.

Atomic Force Microscopy (AFM) Indentation

Young's modulus of microparticles and their corresponding bulk gels were measured using the BioScope Catalyst AFM (Bruker, Calif., USA), equipped with the Zeiss LSM 5 confocal microscope (Germany). Samples were mounted on glass slides using Cell-Tak tissue adhesive, submerged in DPBS for measurements, and visualized using a Zeiss LSM 5 confocal microscope. Measurements were carried out through ~100 nm indentation of the sample surface. Compression moduli were calculated based on the Hertz contact mechanical model (suitable for spherical probes) [9] in the NanoScope Analysis software (version 1.8, Bruker). For the B-GelMA, 3 samples were analyzed (5 beads per samples, characterized 5 times each, total measurements per sample=25), for the GelMA, 3 samples were analyzed (5 spots per samples, characterized 5 times each, total measurements per sample=25).

Rheological Analyses

Oscillatory shear rheology was conducted to characterize the rheological properties of the gels prepared in various forms using an MCR 302 Rheometer (Anton Paar, Graz, Austria). A parallel plate geometry (8 mm with sandblasted measuring plate, PP08/S) was used to load the samples, following equilibration at room temperature. To register the viscoelastic moduli, oscillatory frequency sweep was performed at 0.1-100 rad s-1 under a small oscillatory strain ~0.1% for all samples at 25° C. in the linear viscoelastic region. The gels were maintained hydrated during the experiments (total time ~ 20 min) in an enclosed chamber. The viscoelastic moduli versus angular frequency were registered.

Swelling Analysis

The forced swelling of non-annealed GelMA beads (crosslinked for 120 s through the UV exposure at 10 mW cm$^{-2}$) was investigated by diluting DPBS (1×)-loaded beads with Milli-Q water (1:1 volume ratio) at 37° C. The shrinkage was conducted similarly by adding DPBS (5×). Similar studies were conducted with the physically-crosslinked beads at 4° C. The beads were imaged by brightfield microscopy at predefined time intervals, and their size was measured by analyzing the images using ImageJ (Version 1.52e, National Institute of Health, USA).

In Vitro Characterization of Cellular Function

This section includes cell culture, 3D cell encapsulation, 3D cell seeding, metabolic activity assessment, and Live/Dead assay.

Cell Culture

A standard cell culture incubator (Thermo Fisher Scientific, PA, USA) was used to culture cells in the cell culture flasks under a 5% CO2 atmosphere at 37° C. NIH/3T3 fibroblasts were cultured in DMEM, supplemented with 10% FBS and 1% P/S, typically passaged twice a week. HUVECs were cultured in the endothelial growth medium 2, mixed with SupplementMix and 1% P/S. Every 2-3 days, the media was exchanged for both cell lines. To conduct in vitro characterization of cellular function, fibroblast cells and HUVECs were trypsinized using 0.5% trypsin-EDTA, followed by counting using a hemocytometer and resuspension either in the media (for 3D cell seeding tests), pre-gel solution (for bulk encapsulation), or physically-crosslinked bead suspension (for encapsulation in B-GelMA).

3D Cell Encapsulation

Cell-laden GelMA and B-GelMA samples were prepared by mixing 20 μL of NIH/3T3 fibroblast cell suspension (cell density ~1×10$^6$ in 1 mL DMEM) with 80 μL of GelMA (final concentration ~20% (w/v)) and concentrated bead suspension (~45×10$^4$ of beads per mL of DPBS+PI), respectively, followed by pipetting the mixture on a glass slide between two spacers to form a disc (height ~0.3 mm, diameter ~10 mm), flattened by a cover glass, and crosslinked using UV light exposure at 10 mW cm$^{-2}$ for 2 min (2×10$^5$ cells per sample). The casted gels were gently washed with warm DPBS (37° C.) to remove the unreacted materials, transferred to 6-well plates, and cultured in 2 mL media for up to 14 days with intermittent media exchange every 2 days.

3D Cell Seeding

HUVEC seeding inside the gel samples (discs with height ~0.3 mm, diameter ~ 10 mm) was assessed by gently pipetting 50 μL of the cell suspension (cell density 1×10$^6$ in 1 mL media) on top of the crosslinked gels in a petri dish, immediately stained with the live/dead assay, and imaged. The infiltrated cells inside the gel samples were imaged at various heights using confocal microscopy.

Metabolic Activity Assessment

PrestoBlue® assay was used to assess the cellular metabolic activity on days 1, 3, 7, and 14 based on the manufacturer's protocol. The outcome (fluorescence intensity) was registered using a microplate reader (excitation ~530 nm emission 590 nm, BioTek UV/vis Synnergy 2, VT, USA) and corrected with respect to the background signal of the PrestoBlue®-containing cell-free media.

Live/Dead Assay

A live/dead fluorescence assay was used to assess the cell viability within the hydrogel samples. Briefly, the hydrogels were incubated for 20 min with 1 mL of the staining solution, prepared by adding ethidium homodimer-1 (20 L) and calcein AM (5 μL) to DPBS (10 mL), and imaged using fluorescent microscope (Axio Observer 5, Zeiss, Germany) at excitation/emission wavelengths ~494/515 nm for calcein and 528/617 nm for ethidium homodimer-1.

Statistical Analysis

Measurements were conducted at least in triplicate. The data are reported as mean values t standard deviation. The one-way analysis of variance (ANOVA) was carried out followed by Tukey's multiple comparisons, and statistically significant differences were identified when p-values were lower than 0.05 (*p<0.05), 0.01 (p<0.01), 0.001 (*p<0.001), and 0.0001 (****p<0.0001).

Method Validation

Physical and biological properties of fabricated beaded hydrogels were thoroughly characterized [10]. Furthermore, the results were compared to the bulk hydrogel counterparts [10].

The following references are those noted in "ILLUSTRATIVE METHODS AND MATERIALS USEFUL WITH EMBODIMENTS OF THE INVENTION" immediately above.

[1] T. Kawakatsu, Y. Kikuchi, M. Nakajima, Regular-sized cell creation in microchannel emulsification by visual microprocessing method, J. Am. Oil Chem. Soc. 74 (1997) 317-321.
[2] S. L. Anna. N. Bontoux, H. A. Stone, Formation of dispersions using "flow focusing" in microchannels, Appl. Phys. Lett. 82 (2003) 364-366.
[3] K. Hosokawa, T. Fujii, I. Endo, Handling of picoliter liquid samples in a poly (dimethylsiloxane)-based microfluidic device, Anal. Chem. 71 (1999) 4781-4785.
[4] C. Y. Li, D. K. Wood, C. M. Hsu, S. N. Bhatia, DNA-templated assembly of droplet-derived PEG microtissues, Lab Chip. 11 (2011) 2967-2975.
[5] K. Yue, X. Li, K. Schrobback, A. Sheikhi, N. Annabi. J. Leijten, W. Zhang, Y. S. Zhang, D. W. Hutmacher, T. J. Klein, A. Khademhosseini, Structural analysis of photocrosslinkable methacryloyl-modified protein derivatives, Biomaterials. 139 (2017) 163-171. doi: 10.1016/j.biomaterials.2017.04.050.
[6] J. W. Nichol, S. T. Koshy, H. Bac, C. M. Hwang, S. Yamanlar, A. Khademhosseini, Cell-laden microengineered gelatin methacrylate hydrogels, Biomaterials. 31 (2010) 5536-5544.
[7] A. I. Van Den Bulcke, B. Bogdanov, N. De Rooze, E. H. Schacht. M. Cornelissen, H. Berghmans. Structural and rheological properties of methacrylamide modified gelatin hydrogels, Biomacromolecules. 1 (2000) 31-38.
[8] D. R. Griffin, W. M. Weaver. P. O. Scumpia, D. Di Carlo, T. Segura, Accelerated wound healing by injectable microporous gel scaffolds assembled from annealed building blocks, Nat. Mater. 14 (2015) 737-744. doi:10.1038/nmat4294.
[9] K. L. Johnson, K. L. Johnson, Contact mechanics, Cambridge university press, 1987.
[10] A. Sheikhi, J. de Rutte, R. Haghniaz, O. Akouissi, A. Sohrabi, D. Di Carlo, A. Khademhosseini, Microfluidic-enabled bottom-up hydrogels from annealable naturally-derived protein microbeads, Biomaterials. 2019 February; 192:560-568. doi: 10.1016/j.biomaterials.2018.10.040.

CONCLUSION

This concludes the description of illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein (e.g. Sheikhi et al., Biomaterials. 2019 February; 192:560-568. doi: 10.1016/j.biomaterials.2018.10.040) are hereby incorporated by reference in their entirety for all purposes.

The invention claimed is:

1. A method of forming a hydrogel at a predetermined site comprising:
 (a) performing a precursor formation process on a composition comprising macromolecules having crosslinkable moieties disposed within a liquid;
 (b) incubating the liquid so that the macromolecules are physically crosslinked so as to form a gel emulsion;
 (c) disrupting the gel emulsion so that the liquid comprises an aqueous phase without coalescence;
 (d) delivering the disrupted gel emulsion to the site;
 (e) chemically crosslinking the disrupted gel emulsion in situ so as to form a hydrogel at the site;
 wherein at least one of steps (a), (b), (c), (d) or (e) is performed at a temperature below 10° C.;
 the hydrogel forms a beaded hydrogel scaffold having interconnected pores; and
 the beaded hydrogel scaffold exhibits a compression modulus of at least 10 kPa.

2. The method of claim 1, wherein:
 the precursor formation process is a microfluidic process or an emulsification process; and
 the liquid comprises water, an oil and optionally a surfactant.

3. The method of claim 2, wherein the method includes purifying a beaded hydrogel scaffold precursor composition from the oil and the surfactant so as to form an aqueous solution prior to chemical crosslinking, wherein said purifying occurs at a temperature below 10° C.

4. The method of claim 1, wherein the method includes combining the disrupted gel emulsion with a crosslinking initiator prior to chemical crosslinking.

5. The method of claim 2, wherein fluid flow in the microfluidic process are controlled so as to form hydrogel beads having a median diameter from about 70 μm to about 115 μm.

6. The method of claim 1, wherein the macromolecule comprises:
 a methacryloyl moiety; and/or
 a peptide coupled to the macromolecule.

7. The method of claim 1, wherein the macromolecule comprises a polypeptide.

8. The method of claim 7, wherein the macromolecule comprises a hyaluronic acid, an ethylene glycol, a gelatin, a collagen, an elastin or a fibroin.

9. The method of claim 1, wherein the temperature of the site at which the disrupted gel emulsion is delivered is modulated to be lower than 20° C.

10. The method of claim 1, further comprising seeding mammalian cells within pores in the beaded hydrogel scaffold.

11. The method of claim 10, wherein the mammalian cells exhibit an increasing rate of metabolic activity at 5 days post seeding.

12. The method of claim 1, the macromolecule comprises a gelatin methacryloyl composition.

* * * * *